United States Patent
Abe et al.

(10) Patent No.: US 10,631,797 B2
(45) Date of Patent: Apr. 28, 2020

(54) X-RAY DIAGNOSIS APPARATUS AND CONTROL METHOD

(71) Applicant: Toshiba Medical Systems Corporation, Otawara-shi (JP)

(72) Inventors: Shingo Abe, Nasushiobara (JP); Takuya Sakaguchi, Utsunomiya (JP)

(73) Assignee: Canon Medical Systems Corporation, Otawara-shi (JP)

( * ) Notice: Subject to any disclaimer, the term of this patent is extended or adjusted under 35 U.S.C. 154(b) by 1041 days.

(21) Appl. No.: 14/158,042

(22) Filed: Jan. 17, 2014

(65) Prior Publication Data

US 2014/0135618 A1 May 15, 2014

Related U.S. Application Data

(63) Continuation of application No. PCT/JP2012/068472, filed on Jul. 20, 2012.

(30) Foreign Application Priority Data

Jul. 22, 2011 (JP) .............................. 2011-161407

(51) Int. Cl.
  *A61B 6/12* (2006.01)
  *A61B 6/00* (2006.01)
  (Continued)

(52) U.S. Cl.
  CPC .............. *A61B 6/12* (2013.01); *A61B 5/0402* (2013.01); *A61B 5/746* (2013.01); *A61B 6/463* (2013.01);
  (Continued)

(58) Field of Classification Search
  None
  See application file for complete search history.

(56) References Cited

U.S. PATENT DOCUMENTS 5,042,486 A * 8/1991 Pfeiler .................... A61B 5/06
  324/207.17
5,738,096 A * 4/1998 Ben-Haim .......... A61B 5/0215
  128/899

(Continued)

FOREIGN PATENT DOCUMENTS

JP  1-204650 A  8/1989
JP  2002-526188 A  8/2002

(Continued)

OTHER PUBLICATIONS

International Search Report dated Oct. 2, 2012 for PCT/JP2012/068472 filed on Jul. 20, 2012 with English Translation.

(Continued)

*Primary Examiner* — Katherine L Fernandez
(74) *Attorney, Agent, or Firm* — Oblon, McClelland, Maier & Neustadt, L.L.P.

(57) ABSTRACT

A data creation unit of an X-ray diagnosis apparatus that irradiates a treatment target part of a subject with an X-ray and displays the image data of a transmitted X-ray thereon includes a catheter tip detection unit that detects a catheter tip based on the image data, a tip position information storage unit that stores therein position information of the catheter tip for at least one heartbeat based on a detection result of the catheter tip detection unit as transfer trace information, and a support data creation unit that superimposes the transfer trace information onto the present image data to create support data for catheter treatment.

10 Claims, 14 Drawing Sheets

(51) Int. Cl.
    *A61B 5/0402* (2006.01)
    *A61B 5/00* (2006.01)
    *A61M 25/01* (2006.01)
    *A61B 18/00* (2006.01)
    *A61B 18/14* (2006.01)
    *A61B 34/20* (2016.01)

(52) U.S. Cl.
    CPC ............ *A61B 6/503* (2013.01); *A61B 6/5217* (2013.01); *A61B 6/5241* (2013.01); *A61B 6/5288* (2013.01); *A61M 25/0108* (2013.01); *A61B 18/1492* (2013.01); *A61B 2018/00351* (2013.01); *A61B 2018/00595* (2013.01); *A61B 2018/00839* (2013.01); *A61B 2034/2065* (2016.02)

(56) References Cited

U.S. PATENT DOCUMENTS

| | | | |
|---|---|---|---|
| 6,226,543 | B1 | 5/2001 | Gilboa et al. |
| 6,285,898 | B1* | 9/2001 | Ben-Haim ............ A61B 5/0215 128/899 |
| 6,711,429 | B1 | 3/2004 | Gilboa et al. |
| 2001/0031985 | A1 | 10/2001 | Gilboa et al. |
| 2003/0074011 | A1* | 4/2003 | Gilboa .................... A61B 5/06 606/130 |
| 2004/0006268 | A1 | 1/2004 | Gilboa et al. |
| 2006/0257006 | A1* | 11/2006 | Bredno .................... A61B 6/12 382/128 |
| 2007/0232896 | A1 | 10/2007 | Gilboa et al. |
| 2008/0139930 | A1* | 6/2008 | Weese .................... A61B 5/042 600/424 |
| 2008/0312528 | A1* | 12/2008 | Bertolina ................ A61B 6/12 600/426 |
| 2010/0016709 | A1 | 1/2010 | Gilboa et al. |
| 2010/0097373 | A1* | 4/2010 | Besz ....................... A61B 5/06 345/419 |
| 2010/0324413 | A1* | 12/2010 | Tetsuka ................ A61B 5/0402 600/424 |
| 2011/0058647 | A1* | 3/2011 | Star-Lack ........... G01N 23/046 378/23 |
| 2012/0071751 | A1* | 3/2012 | Sra ......................... A61B 6/12 600/424 |
| 2012/0300903 | A1* | 11/2012 | Yao ......................... A61B 6/12 378/62 |

FOREIGN PATENT DOCUMENTS

| | | |
|---|---|---|
| JP | 2008-528165 A | 7/2008 |
| JP | 2009-106633 A | 5/2009 |
| JP | 2010-012097 A | 1/2010 |

OTHER PUBLICATIONS

International Written Opinion dated Oct. 2, 2012 for PCT/JP2012/068472 filed on Jul. 20, 2012.

U.S. Appl. No. 12/797,040, filed Jun. 9, 2010, Publication No. 2010-0324413, Tetsuka et al.

* cited by examiner

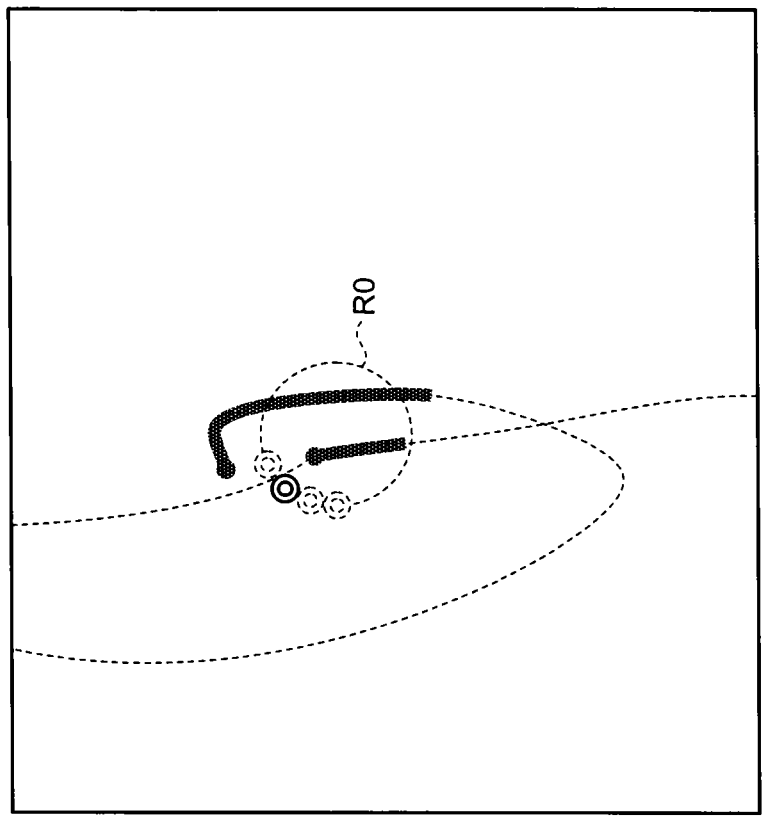
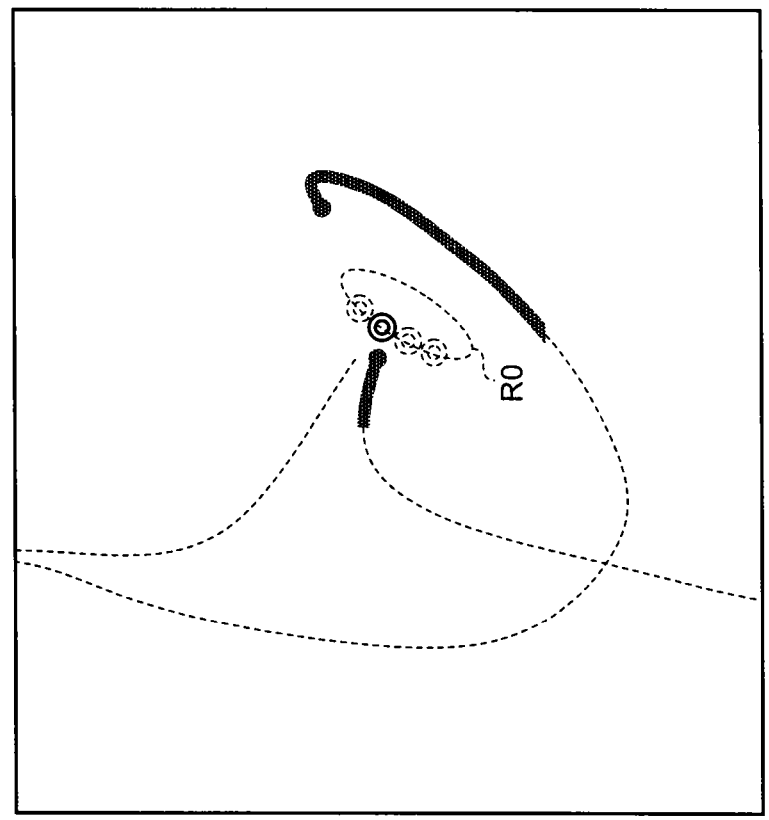
FIG.14

X-RAY DIAGNOSIS APPARATUS AND CONTROL METHOD

CROSS-REFERENCE TO RELATED APPLICATIONS

This application is a continuation of PCT international application Ser. No. PCT/JP2012/068472 filed on Jul. 20, 2012 which designates the United States, incorporated herein by reference, and which claims the benefit of priority from Japanese Patent Application No. 2011-161407, filed on Jul. 22, 2011, the entire contents of which are incorporated herein by reference.

FIELD

Embodiments described herein relate generally to an X-ray diagnosis apparatus and control method that can create effective support data for catheter treatment performed while X-ray image data is observed.

BACKGROUND

A medical image diagnosis using an X-ray diagnosis apparatus, an X-ray CT apparatus, or the like has made rapid progress with the expansion of the computer technologies to be indispensable in medical care today. In particular, an X-ray image diagnosis in the cardiovascular field that has made progress with the expansion of the catheter manipulation is widely used for various arteries and veins in a human body including the cardiovascular system.

The X-ray diagnosis apparatus on the purpose of diagnosis in the cardiovascular field includes an X-ray generation unit and an X-ray detection unit (hereinafter, referred to as an imaging system), a retention unit such as a C-arm that retains the imaging system, and a couchtop that mounts a subject thereon. The X-ray diagnosis apparatus transfers the couchtop or the imaging system installed on the retention unit described above in an intended direction, thereby enabling radiography on a treatment target part of the subject from the most suitable direction.

An example of catheter treatment performed while X-ray image data created by radiography described above is observed is a catheter ablation that performs treatment for such as arrhythmia by ablating a stimulus conduction pathway that exists on the surface of the cardiac muscle using high-frequency current.

In the catheter ablation on the purpose of treating arrhythmia and the like, the following method is used to perform radical treatment for arrhythmia: at first, a tip of a catheter for measurement having a ring-shaped multi-electrode is inserted in a cardiac cavity; then, myocardial potential generated at pulmonary vein opening on the surface of the cardiac muscle, for example, is measured, thereby specifying a position of the left atrium—pulmonary vein stimulus conduction pathway (hereinafter, referred to as a treatment target part) that induces is arrhythmia; subsequently, the treatment target part is ablated using the tip of the catheter for treatment inserted in the cardiac cavity described above.

In the catheter ablation in which the tip of the catheter for treatment contacts the treatment target part that exists on the surface of or in the vicinity of the cardiac muscle and high-frequency current is provided to the treatment target part through a chip provided on the tip to perform ablation, placement of the tip of the catheter for treatment against the treatment target part of which position is specified by the catheter for measurement has been performed while the image data displayed almost in real time is observed.

However, in the radiography in which the catheter for treatment inserted in the cardiac cavity is required to be displayed, the surface of the cardiac muscle can be hardly represented some times due to use of a contrast agent. Therefore, there has been a problem that placing the tip of the catheter for treatment accurately to a diagnosis target part that moves along with heartbeats of the heart is extraordinarily difficult.

BRIEF DESCRIPTION OF THE DRAWINGS

FIG. 14 is a diagram illustrating a specific example of the support data for catheter treatment created in another embodiment.

DETAILED DESCRIPTION

An X-ray diagnosis apparatus configured to irradiate a treatment target part of a subject with an X-ray to display image data of a transmitted X-ray thereon includes a detection unit, a storage unit, a support data creation unit, and a display unit. The detection unit is configured to detect a tip of a catheter based on the image data. The storage unit is configured to store therein transfer trace information of the tip of the catheter for at least one heartbeat based on a detection result of the detection unit. The support data creation unit is configured to superimpose the transfer trace information onto the present image data to create support data for catheter treatment. The display unit is configured to display the support data for catheter treatment.

Embodiments disclosed in the present disclosure are described below with reference to the accompanying drawings.

Embodiments

In the X-ray diagnosis apparatus according to the embodiments, at first, the myocardial potential is measured using a catheter for measuring the myocardial potential (hereinafter, referred to as a catheter for measurement) inserted in the heart of a subject, thereby specifying the position of the treatment target part, to which radiography in a reference data collection mode in a predetermined cardiac cycle is performed in a state in which a tip of the catheter for measurement is placed in the treatment target part, whereby the tip position information of the catheter for measurement (tip transfer trace information) having a heartbeat time phase as supplementary information is collected.

Subsequently, on the purpose of ablation treatment of the treatment target part, radiography in the support data creation mode and measurement of electrocardiographic waveforms are performed in a state in which the tip of the catheter for treatment that has been inserted in the heart of the subject is placed in the vicinity of the treatment target part. The tip position information of the catheter for measurement collected here in the heartbeat time phase that is the same as or the closest to the heartbeat time phase of the image data obtained as above is superimposed onto the image data described above, thereby creating the support data for catheter treatment effective in ablation treatment.

In the embodiment, an example in which arrhythmia is removed by performing ablation treatment using the catheter for treatment to the treatment target part on the surface of the cardiac muscle will be described. However, treatment using the catheter for treatment is not limited to the example described above.

Figure 1:
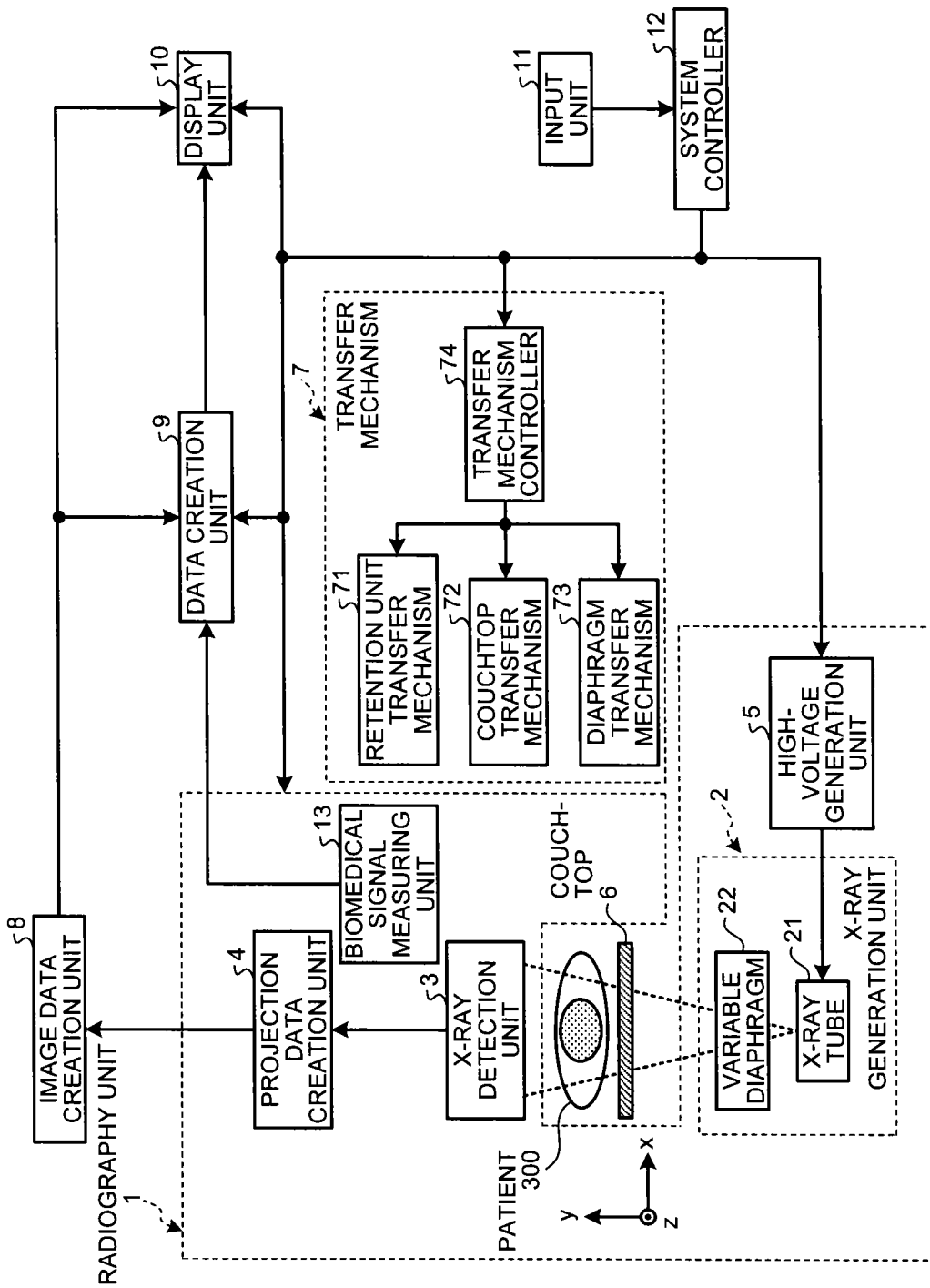
FIG. 1 is a block diagram illustrating an entire structure of an X-ray diagnosis apparatus according to an embodiment.
Figure 2:
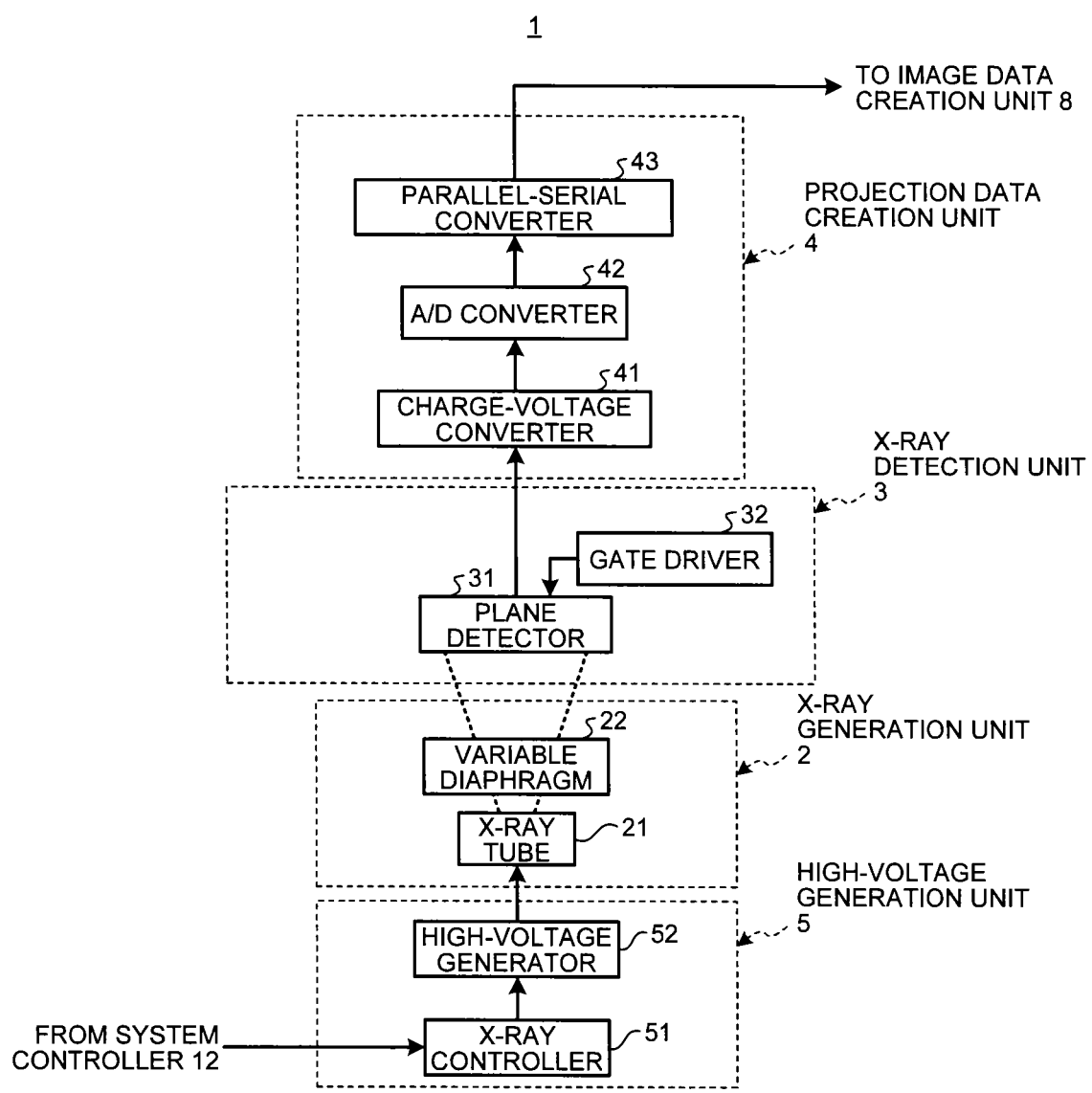
FIG. 2 is a block diagram illustrating a specific structure of a radiography unit included in the X-ray diagnosis apparatus according to the embodiment.
Figure 3:
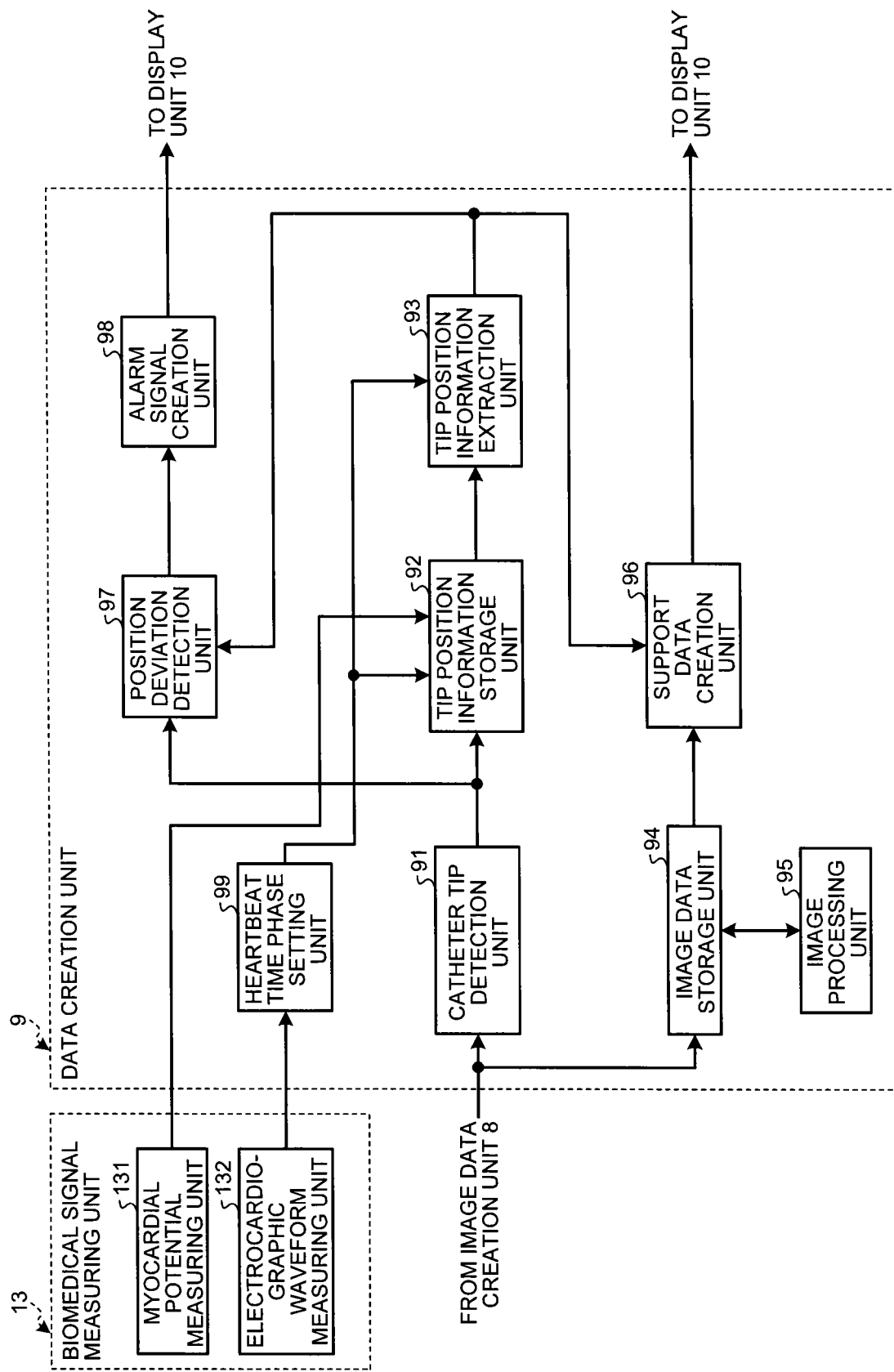
FIG. 3 is a block diagram illustrating a specific structure of a data creation unit included in the X-ray diagnosis apparatus according to the embodiment.

The structure and functions of the X-ray diagnosis apparatus according to the embodiment will be described with reference to FIG. 1 through FIG. 7. FIG. 1 is a block diagram illustrating the entire structure of the X-ray diagnosis apparatus according to the embodiment. FIG. 2 is a block diagram illustrating the specific structure of a radiography unit included in the X-ray diagnosis apparatus according to the embodiment, while FIG. 3 is a block diagram illustrating the specific structure of a data creation unit included in the X-ray diagnosis apparatus according to the embodiment.

An X-ray diagnosis apparatus 100 illustrated in FIG. 1 includes a radiography unit 1, a retention unit, a couchtop 6, a transfer mechanism 7, an image data creation unit 8, a data creation unit 9, and further includes a display unit 10, an input unit 11, a system controller 12, and a biomedical signal measuring unit 13. The radiography unit 1 irradiates a scan field including the treatment target part of a subject 300 with arrhythmia with an X-ray in the reference data collection mode and the support data creation mode to detect the X-ray transmitted through the scan field, thereby creating projection data. The retention unit (not illustrated) retains the imaging system that performs X-ray irradiation and X-ray detection described above. The couchtop 6 carries the subject 300. The transfer mechanism 7 transfers the retention unit to which the imaging system is installed and the couchtop 6 that carries the subject 300, and further transfers a variable diaphragm 22 provided in an X-ray generation unit 2 described later to an intended position. The image data creation unit 8 creates image data using projection data in the reference data collection mode and the support data creation mode that is output from the radiography unit 1. The data creation unit 9 detects the tip position information of the catheter for measurement based on the image data in the reference data collection mode collected in a state in which the tip of the catheter for measurement is placed on a preferred position of the treatment target part or in the vicinity thereof to superimpose the tip position information of the catheter for measurement onto the image data collected through radiography in the support data creation mode on the subject 300 to which the catheter for treatment is inserted, thereby creating the support data for catheter treatment. The display unit 10 displays the support data for catheter treatment created in the data creation unit 9 or an alarm signal created in an alarm signal creation unit 98 described later, for example. The input unit 11 performs an input of information of the subject, selection of the reference data collection mode or the support data creation mode, settings of radiography conditions or image data creation conditions in each of the modes, settings of creation conditions or display conditions of the support data for catheter treatment, or an input of various instruction signals, for example. The system controller 12 controls overall the units included in the X-ray diagnosis apparatus 100 described above. The biomedical signal measuring unit 13 measures electrocardiographic waveforms or myocardial potential of the subject 300.

As illustrated in FIG. 1, the radiography unit 1 includes the X-ray generation unit 2 and an X-ray detection unit 3 that constitute the imaging system, a projection data creation unit 4, and a high-voltage generation unit 5 to have a function to irradiate the scan field of the subject 300 with an X-ray and a function to create projection data based on the X-ray transmitted through the scan field.

FIG. 2 is a block diagram illustrating the specific structure of the units provided in the radiography unit 1 described above. The X-ray generation unit 2 includes an X-ray tube 21 that irradiate the scan field of the subject 300 with the X-ray and the variable diaphragm 22 that forms an X-ray cone-beam of a predetermined range for the X-ray irradiated from the X-ray tube 21. The X-ray tube 21 is a vacuum tube that accelerates thermions generated from a heated cathode (filament) using high voltage DC provided from the high-voltage generation unit 5 to be collided with a tungsten anode, thereby generating an X-ray.

The variable diaphragm 22 is used on the purpose of reduction of exposed dose on the subject 300 and improvement of the quality of image data. The variable diaphragm 22 has a diaphragm blade (upper blade), a lower blade, and a compensation filter (none of them illustrated). The diaphragm blade limits the X-ray irradiated from the X-ray tube 21 to a predetermined irradiation field. The lower blade moves in conjunction with the diaphragm blade to reduce scattered X-rays or leakage radiation dose. The compensation filter selectively reduces the X-ray transmitted through a medium with low absorption, thereby avoiding halation.

In particular, the X-ray irradiation range in the support data creation mode according to the embodiment is determined by the diaphragm blade of the variable diaphragm 22 of which position is controlled in accordance with the tip position information of the catheter for measurement detected in the reference data collection mode. By limiting the X-ray irradiation range to the treatment target part close to the tip of the catheter for measurement, exposed dose on the subject 300 can be reduced.

The X-ray detection unit 3 has two methods: a method in which an image intensifier and an X-ray TV are used and a method in which a plane detector is used. The plane detector has two methods: a method in which the X-ray is directly converted into electric charge and a method in which the X-ray is converted into electric charge after converted into light. The X-ray detection unit 3 having the plane detector that can directly convert the X-ray into electric charge will be described. However, the embodiment is not limited to this example.

Specifically, as illustrated in FIG. 2, the X-ray detection unit 3 according to the embodiment has a plane detector 31 that detects the X-ray transmitted through the subject 300 and a gate driver 32 that provides driving signals to read out the X-ray detected in the plane detector 31 as signal charge.

The plane detector 31 is structured so that miner detecting elements are arranged in two-dimensional array in a column direction and a line direction. Each of the detecting elements has a photoelectric film that perceives the X-ray to generate signal charge depending on an amount of an incident X-ray, a charge accumulation capacitor that accumulates the signal charge generated in the photoelectric film, and a thin-film transistor (TFT) that reads out the signal charge accumulated in the charge accumulation capacitor at a predetermined timing (none of them illustrated).

The projection data creation unit 4 has a charge-voltage converter 41, an A/D converter 42, and a parallel-serial converter 43. The charge-voltage converter 41 converts signal charge that has been read out in parallel in a line direction, for example, from the plane detector 31 described above into voltage. The A/D converter 42 converts an output from the charge-voltage converter 41 into digital signals (data elements of the projection data). The parallel-serial converter 43 converts the data elements that have been digital-converted described above into time-series data elements. The time-series data elements that have been output from the parallel-serial converter 43 are provided to the image data creation unit 8.

The high-voltage generation unit 5 includes a high-voltage generator 52 and an X-ray controller 51. The high-voltage generator 52 generates high voltage to be applied between the anode and the cathode in order to accelerate thermions generated from the cathode of the X-ray tube 21. The X-ray controller 51 controls tube current, tube voltage, applied time, applied timing, and a repetition frequency of the X-ray irradiation, for example, in the high-voltage generator 52 based on the X-ray irradiation conditions in the reference data collection mode and the support data creation mode provided from the system controller 12. In particular in the embodiment, the repetition frequency of the X-ray irradiation in the reference data collection mode can be set higher than the repetition frequency of the X-ray irradiation in the support data creation mode, thereby increasing a frame rate of the image data in order to accurately detect the tip position information of the catheter for measurement that periodically changes along with heartbeats.

With reference to FIG. 1 again, the transfer mechanism 7 includes a retention unit transfer mechanism 71, a couchtop transfer mechanism 72, a diaphragm transfer mechanism 73, and a transfer mechanism controller 74. The retention unit transfer mechanism 71 rotates or moves the retention unit (not illustrated) to which the X-ray generation unit 2 and the X-ray detection unit 3 (the imaging system) are installed around the subject 300. The couchtop transfer mechanism 72 moves the couchtop 6 in a direction of the body axis of the subject 300 (the direction z in FIG. 1) and in a direction perpendicular to the body axis (the directions x and y in FIG. 1). The diaphragm transfer mechanism 73 moves the diaphragm blades of the variable diaphragm 22 provided in the X-ray generation unit 2 to a predetermined position. The transfer mechanism controller 74 controls the retention unit transfer mechanism 71, the couchtop transfer mechanism 72, and the diaphragm transfer mechanism 73.

The transfer mechanism controller 74 provides a transfer control signal created in accordance with an imaging system transfer instruction signal provided from the input unit 11 through the system controller 12 to the retention unit transfer mechanism 71 to rotate or move the retention unit to which the imaging system is installed around the subject 300, thereby setting a position and a direction for radiography.

In the same manner, the transfer mechanism controller 74 provides a transfer control signal created in accordance with a couchtop transfer instruction signal provided from the input unit 11 through the system controller 12 to the couchtop transfer mechanism 72 to move the couchtop 6 in parallel in the direction of the body axis of the subject 300 or in the direction perpendicular to the body axis, thereby setting the center of the scan field.

Furthermore, the transfer mechanism controller 74 provides a transfer control signal created in accordance with the tip position information of the catheter for measurement provided from a tip position information storage unit 92 of the data creation unit 9 through the system controller 12 to the diaphragm transfer mechanism 73 to move a plurality of diaphragm blades provided in the variable diaphragm 22 of the X-ray generation unit 2 to a predetermined position, thereby limiting the X-ray irradiation field in the support data creation mode to the treatment target part close to the tip of the catheter for measurement.

The image data creation unit 8 has a projection data storage unit not illustrated in which data elements of the projection data that have been output in a time-series manner from the parallel-serial converter 43 of the projection data creation unit 4 in radiography in the reference data collection mode and the support data creation mode are stored in series in a corresponding manner in a column direction and a line direction of the detecting element to create two dimensional image data.

Now, the specific structure and functions of the data creation unit 9 will be described with reference to FIGS. 3 to 5. FIG. 3 is a block diagram illustrating the specific structure of the data creation unit 9, while FIG. 4 is a block diagram illustrating a specific structure of a catheter tip detection unit 91 included in the data creation unit 9.

As illustrated in FIG. 3, the data creation unit 9 has the catheter tip detection unit 91, the tip position information storage unit 92, a tip position information extraction unit 93, an image data storage unit 94, an image processing unit 95, a support data creation unit 96, and further includes a position deviation detection unit 97, the alarm signal creation unit 98, and a heartbeat time phase setting unit 99.

Figure 4:
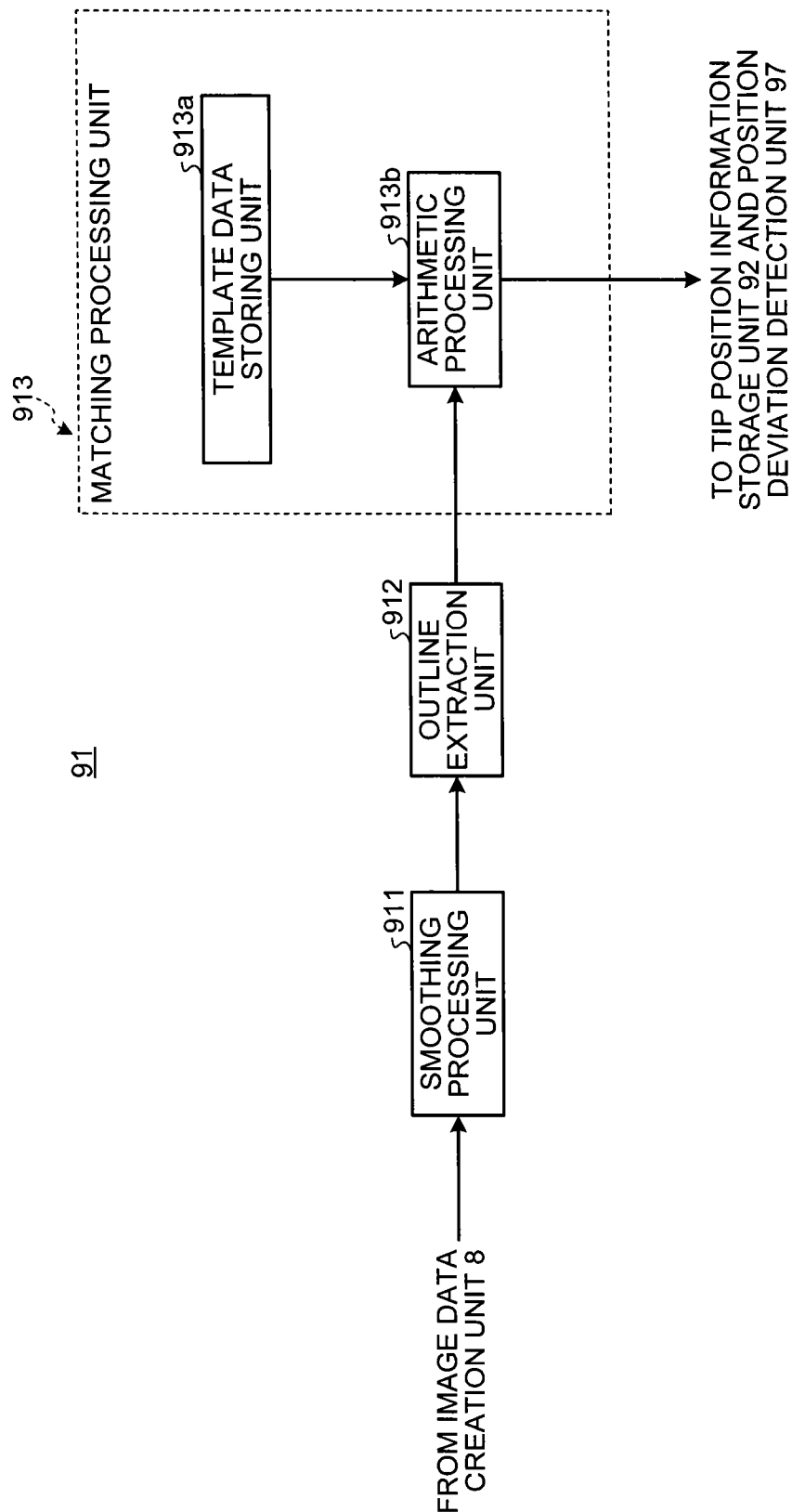
FIG. 4 is a block diagram illustrating a specific structure of a catheter tip detection unit included in the data creation unit according to the embodiment.

As illustrated in FIG. 4, the catheter tip detection unit 91 has a smoothing processing unit 911, an outline extraction unit 912, and a matching processing unit 913, for example. The smoothing processing unit 911 performs filtering processing on the image data provided from the image data creation unit 8 in radiography in the reference data collection mode and the support data creation mode on the purpose of smoothing to remove unwanted noise components. The outline extraction unit 912 performs filtering processing on the image data smoothed as described above on the purpose of highlighting an outline to extract the outline of the catheter for measurement represented on the image data in the reference data collection mode, or the outline of the catheter for treatment represented on the image data in the support data creation mode.

The matching processing unit 913 includes a template data storing unit 913a and an arithmetic processing unit 913b. In the template data storing unit 913a, three-dimensional template data representing the tip shapes of various catheters are stored in advance with the catheter identification information as supplementary information. The arithmetic processing unit 913b reads out the template data corresponding to the catheter for measurement used in the reference data collection mode and the catheter for treatment used in the support data creation mode out of various template data stored in the template data storing unit 913a based on the catheter identification information described above to detect the tip position information of the catheter for measurement and the catheter for treatment (tip transfer trace information) through pattern matching processing between the template data obtained and the image data after the outline extraction provided from the outline extraction unit 912.

If a plurality pieces of different position information are detected in the pattern matching processing described above, it is desirable that the position information closest to the tip position information of the adjacent heartbeat time phase already detected, is selected as the tip position information of the catheter for measurement and the catheter for treatment in the heartbeat time phase.

The tip position information of the catheter for measurement (tip transfer trace information) based on the time-series image data collected in a predetermined heartbeat period (e.g., one heartbeat period) in the reference data collection mode is stored in the tip position information storage unit 92 illustrated in FIG. 3 with heartbeat time phase information of the subject 300 provided from the heartbeat time phase setting unit 99 described later. That is to say, in the tip position information storage unit 92, the tip position information of the catheter for measurement detected in a time-series manner in the heartbeat time phase having an equal time interval as that of an irradiation period of the X-ray in the reference data collection mode (tip transfer trace information) is stored in series with the heartbeat time phase as supplementary information.

In this respect, in the tip position information storage unit 92, myocardial potential measured in a myocardial potential measuring unit 131 described later included in the biomedical signal measuring unit 13 is provided and only the tip position information of a predetermined heartbeat period (one heartbeat period) in which the myocardial potential larger than a threshold α that has been set in advance is measured consecutively is stored with the heartbeat time phase. The tip position information detected during a time period smaller than the threshold α (i.e., a time period while the tip of the catheter for measurement does not contact the treatment target part or the cardiac muscle) is removed.

The tip position information of the catheter for treatment detected based on the image data in the support data creation mode is provided to the position deviation detection unit 97 to be used for position deviation detection between the tip of the catheter for measurement and the tip of the catheter for treatment.

The tip position information extraction unit 93 illustrated in FIG. 3 receives the information of the heartbeat time phase of the subject 300 provided from the heartbeat time phase setting unit 99 in the support data creation mode and extracts the tip position information of the catheter for measurement detected in the heartbeat time phase in the reference data collection mode that is the same as or the closest to the heartbeat time phase received above, out of the various tip position information stored in the tip position information storage unit 92.

The image data storage unit 94 once stores the image data provided from the image data creation unit 8 in the support data creation mode. The image processing unit 95 performs image processing on the image data stored in the image data storage unit 94 almost in real time on the purpose of noise reduction or highlighting the outline, for example. Then, the image data after the processing is stored in the image data storage unit 94 again.

The support data creation unit 96 includes a data addition unit not illustrated and superimposes the tip position information of the catheter for measurement in the reference data collection mode provided from the tip position information extraction unit 93 onto the image data in the support data creation mode provided from the image data storage unit 94, thereby creating the support data for catheter treatment. That is to say, the data addition unit receives the image data after the processing provided from the image data storage unit 94 in the support data creation mode. Subsequently, the tip position information extraction unit 93 superimposes the tip position information of the catheter for measurement with the heartbeat time phase that is the same as or the closest to the heartbeat time phase of the subject 300 when the image data extracted by the tip position information extraction unit 93 out of the various tip position information stored in the tip position information storage unit 92 is collected (hereinafter, referred to as a heartbeat time phase of the image data for a simple explanation) as supplementary information onto the image data in the support data creation mode, thereby creating the support data for catheter treatment.

Figure 5:
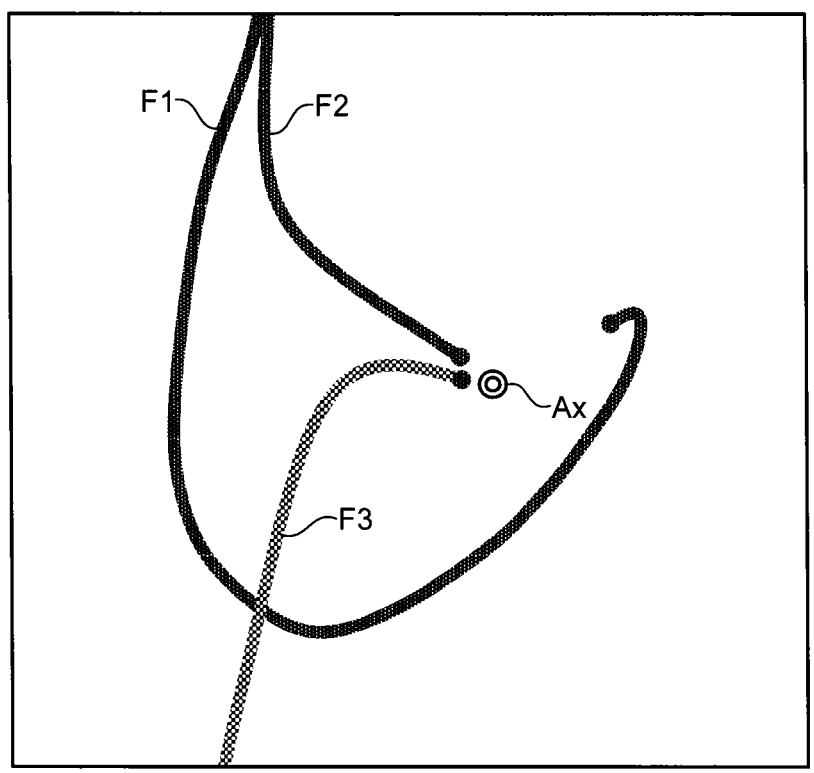
FIG. 5 is a diagram illustrating a specific example of support data for catheter treatment created in a support data creation unit according to the embodiment.

FIG. 5 is a diagram illustrating a specific example of support data for catheter treatment created by the support data creation unit 96 described above. As described above, the support data for catheter treatment is created by superimposing the tip position information of the catheter for measurement Ax corresponding to the heartbeat time phase of the image data extracted from the tip position information storage unit 92 onto the image data in the support data creation mode representing catheters for measurement F1 and F2 having an electrode for measurement at the tip thereof as the myocardial potential measuring unit 131, and the catheter for treatment F3 having an electrode for ablation at the tip thereof.

With reference to FIG. 3 again, the position deviation detection unit 97 of the data creation unit 9 includes a distance measuring unit not illustrated. When the support data for catheter treatment described above is created in the support data creation mode, the position deviation detection unit 97 detects position deviation between the tip of the catheter for measurement and the tip of the catheter for treatment at the same heartbeat time phase based on the tip position information of the catheter for treatment detected by the catheter tip detection unit 91 in accordance with the image data in the support data creation mode provided from the image data creation unit 8 almost in real time, and the tip position information of the catheter for measurement with the heartbeat time phase that is the same as or the closest to the heartbeat time phase of the image data provided from the tip position information extraction unit 93 as supplementary information. The distance measuring unit, for example, measures the distance between the tips of the catheters based on the tip position coordinate of the catheter for treatment provided from the catheter tip detection unit 91 in the support data creation mode and the tip position coordinate of the catheter for measurement provided from the tip position information extraction unit 93.

The alarm signal creation unit 98 has a data comparison unit and an alarm message creation unit not illustrated. The data comparison unit compares a detection result of position deviation provided from the position deviation detection unit 97 and a threshold β that has been set in advance. If the position deviation between the tip of the catheter for measurement and the tip of the catheter for treatment at the same heartbeat time phase is larger than the threshold β, the alarm message creation unit creates an alarm message such as "The tip of the catheter for treatment is apart from the treatment target part. Please set it again." in a predetermined format.

The heartbeat time phase setting unit 99 sets the heartbeat time phase in the reference data collection mode and the support data creation mode based on the electrocardiographic waveforms of the subject provided from an electrocardiographic waveform measuring unit 132 included in the biomedical signal measuring unit 13. Specifically, the heartbeat time phase setting unit 99 detects an R wave of the electrocardiographic waveforms provided from the electrocardiographic waveform measuring unit 132, subsequently divides an interval of two R waves adjacent to each other in a time direction (R-R interval) by a predetermined time interval Δτ, thereby setting the heartbeat time phases (e.g., heartbeat time phases P1 through PN described later). Then, the heartbeat time phase that has been set in the reference data collection mode is provided to the tip position information storage unit 92, while the heartbeat time phase that has been set in the support data creation mode is provided to the tip position information extraction unit 93.

After that, the display unit 10 illustrated in FIG. 1 includes a display data creation unit, a data conversion unit, and a monitor not illustrated. The display data creation unit converts the support data for catheter treatment created in the support data creation unit 96 of the data creation unit 9 into a predetermined display format and further adds the alarm message (alarm signal) provided from the alarm signal creation unit 98, the subject information, or the like as necessary to create display data. Then, the data conversion unit performs conversion processing such as D/A conversion or television format conversion on the display data created by the display data creation unit to be displayed on the monitor.

By displaying the tip position information of the catheter for measurement included in the display data described above using a color tone, brightness, a degree of transparency, and the like different from the image data in the support data creation mode in which the tip position information is superimposed, the position relationship with respect to the tip of the catheter for treatment is clarified and when unacceptable position deviation occurs, the position deviation of the tip of the catheter for treatment can be readily corrected.

The input unit 11 is an interactive interface that includes an input device such as a display panel, a keyboard, a track ball, a joy stick, or a mouse. The input unit 11 performs an input of information of the subject, selection of the reference data collection mode or the support data creation mode, settings of radiography conditions including the X-ray irradiation conditions or image data creation conditions in each of the modes, settings of creation conditions or display conditions of the support data for catheter treatment, settings of the threshold α and the threshold β, an input of various instruction signals, or the like using the display panel or other input device described above.

The system controller 12 includes a CPU and a storage circuit not illustrated. Various pieces of information that have been input, set, or selected through the input unit 11 are stored in the storage circuit described above. The CPU controls the units included in the X-ray diagnosis apparatus 100 described above based on these pieces of information to perform creation of the image data in the reference data collection mode and the support data creation mode, detection of the tip position information of the catheter for measurement based on the image data in the reference data collection mode, composition of the image data in the support data creation mode representing the catheter for treatment and the tip position information of the catheter for measurement described above, thereby creating the support data for catheter treatment.

As illustrated in FIG. 3, the biomedical signal measuring unit 13 includes the myocardial potential measuring unit 131 and the electrocardiographic waveform measuring unit 132. The myocardial potential measuring unit 131 is mounted at the tip of the catheter for measurement that is placed on the treatment target part of the cardiac muscle to measure the myocardial potential generated by the treatment target part in the reference data collection mode. The electrocardiographic waveform measuring unit 132 measures the electrocardiographic waveforms of the subject 300 in the reference data collection mode and the support data creation mode.

The myocardial potential measuring unit 131 includes the electrode for measurement that measures potential on the surface of the cardiac muscle (refer to FIG. 5) and is provided at the tip of the catheter for measurement that is inserted in the heart of the subject 300 on the purpose of measurement of the myocardial potential. By measuring the myocardial potential generated in the treatment target part using the myocardial potential measuring unit 131, the treatment target part can be located. The tip position information of the catheter for measurement in a predetermined heartbeat period (one heartbeat period) in which the myocardial potential measured here has a larger amplitude than the threshold α is stored in the tip position information storage unit 92.

The electrocardiographic waveform measuring unit 132 includes an electrode for measurement mounted on a body surface of the subject 300 to measure the electrocardiographic waveforms thereof, an amplifier circuit that amplifies the electrocardiographic waveforms measured by the electrode for measurement to a predetermined amplitude, and an A/D converter that converts the electrocardiographic waveforms amplified into digital signals (none of them illustrated).

Figure 6:
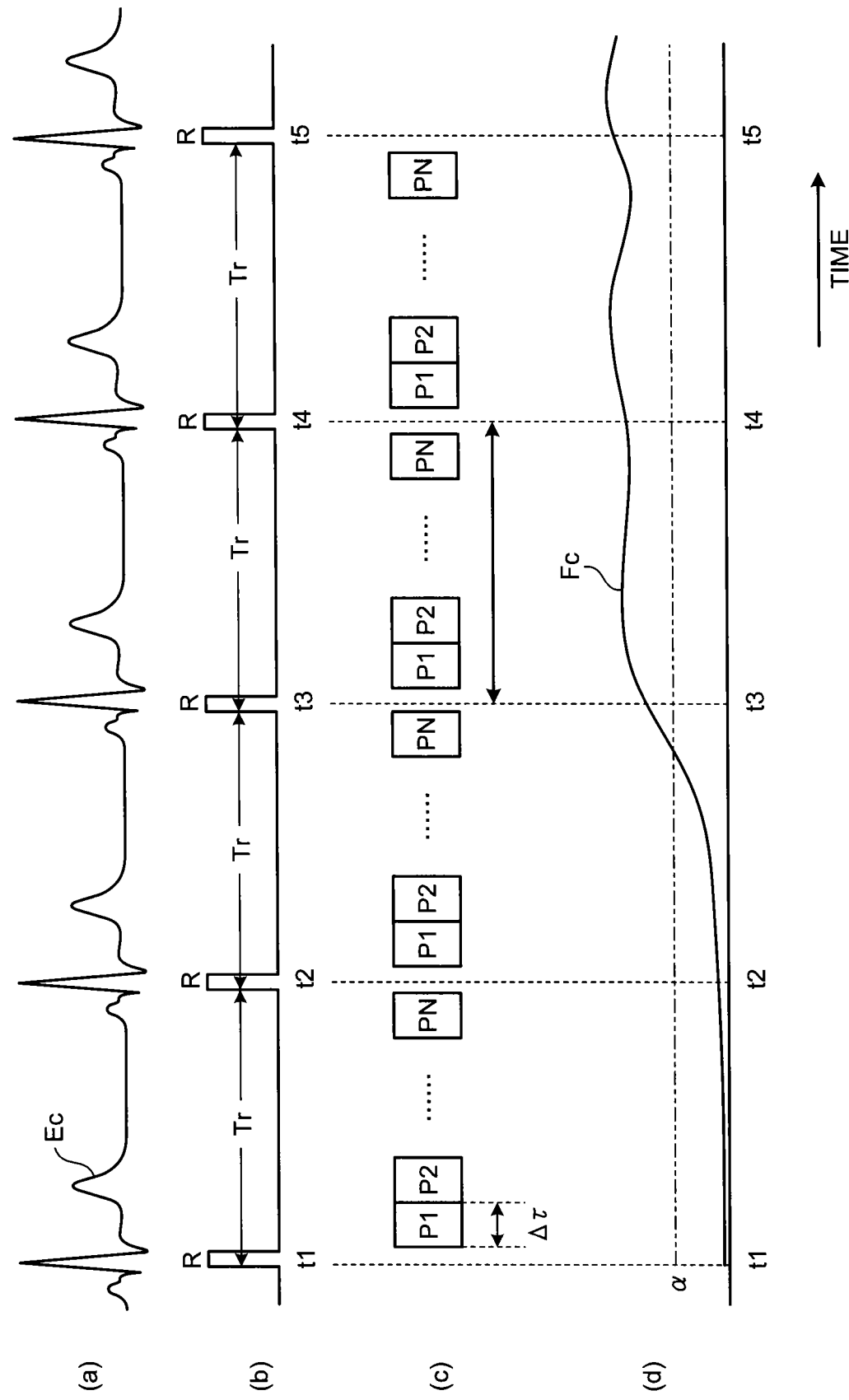
FIG. 6 is a diagram for explaining tip position information of catheter for measurement stored in a tip position information storage unit according to the embodiment.

The myocardial potential and the electrocardiographic waveforms measured in the reference data collection mode described above and the tip position information of the catheter for measurement stored in the tip position information storage unit 92 based on the measurement data thereof will now be described with reference to FIG. 6. FIG. 6A represents an electrocardiographic waveforms Ec of the subject 300 measured by the electrocardiographic waveform measuring unit 132 of the biomedical signal measuring unit 13. FIG. 6B represents the R wave and the R-R interval Tr detected by the heartbeat time phase setting unit 99 based on the electrocardiographic waveforms Ec. FIG. 6C represents the heartbeat time phases P1 through PN that have been set by the heartbeat time phase setting unit 99 by dividing each of the R-R intervals Tr by the time interval Δτ. FIG. 6D represents the myocardial potential Fc and the threshold α in the treatment target part of the subject 300 measured by the myocardial potential measuring unit 131 of the biomedical signal measuring unit 13.

In this respect, in the tip position information storage unit 92, the tip position information of the catheter for measurement in the heartbeat time phases P1 through PN detected by the catheter tip detection unit 91 in a predetermined heartbeat period (e.g., one heartbeat period of a time period [t3-t4]) at a time t3 or later in which the myocardial potential Fc in the reference data collection mode is larger than the threshold α that has been set in advance is stored with the heartbeat time phase as supplementary information.

Figure 7:
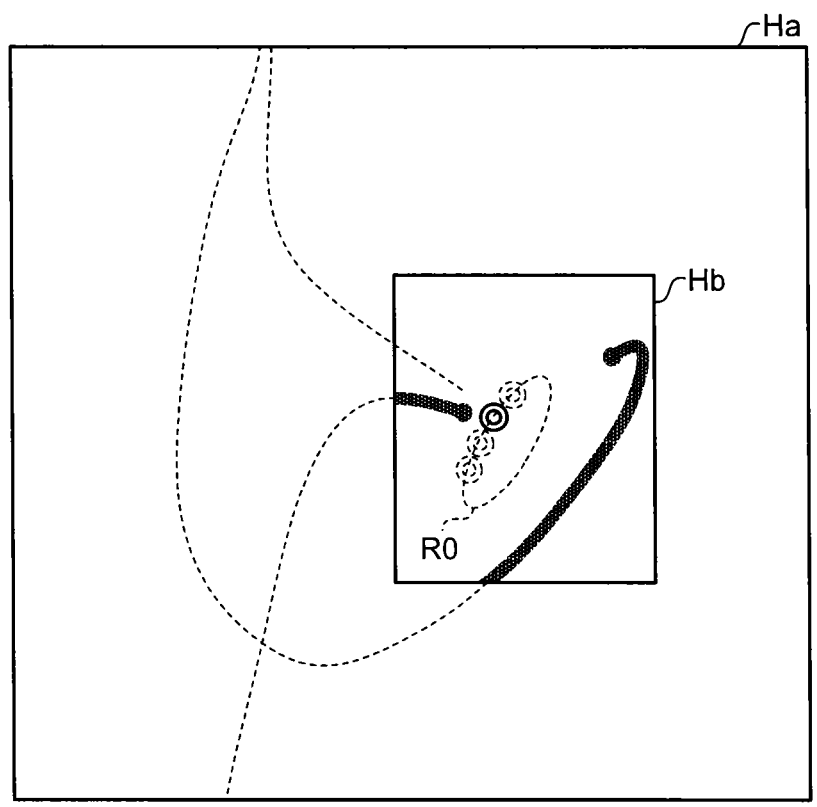
FIG. 7 is a diagram for explaining an X-ray irradiation field that is set in a support data creation mode according to the embodiment.

The X-ray irradiation field that is set in radiography in the support data creation mode will be now described below with reference to FIG. 7. Ha illustrated in FIG. 7 represents the X-ray irradiation field in radiography in the reference data collection mode, while Hb represents the X-ray irradiation field in radiography in the support data creation mode.

The support data for catheter treatment illustrated in FIG. 5 is based on the image data collected through radiography in the support data creation mode having an X-ray irradiation field equal to the X-ray irradiation field in radiography in the reference data collection mode. In the embodiment, as described above, the X-ray irradiation field in the support data creation mode can be limited to an area around the treatment target part.

In this respect, the transfer mechanism controller 74 of the transfer mechanism 7 provides the transfer control signal created in accordance with the tip position information of the catheter for measurement provided from the tip position information storage unit 92 of the data creation unit 9 through the system controller 12 to the diaphragm transfer mechanism 73. Subsequently, the diaphragm transfer mechanism 73 that has received the transfer control signal moves each of a plurality of diaphragm blades included in the variable diaphragm 22 of the X-ray generation unit 2 to a predetermined position, whereby, for example, the X-ray irradiation field in the support data creation mode is set for the relatively narrow field Hb including a closed curve R0 representing the tip of the catheter for measurement placed in the treatment target part in the heartbeat time phases P1 through PN will be set.

Detection/Storage Procedures of the Tip Position Information

Detection and storage procedures of the tip position information of the catheter for measurement in the reference data collection mode according to the embodiment will now be described with reference to the flowchart illustrated in FIG. 8.

Figure 8:
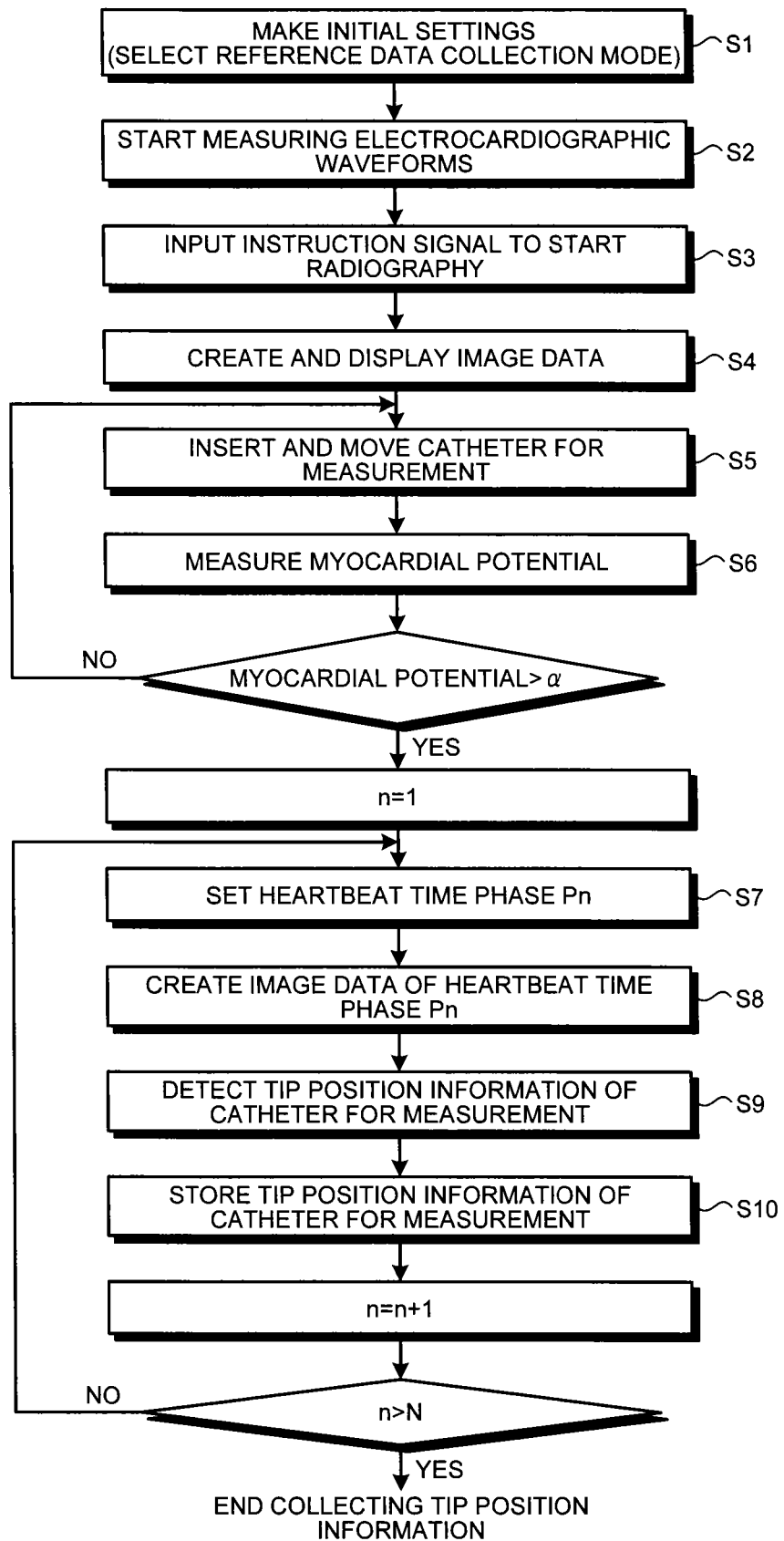
FIG. 8 is a flowchart illustrating detection and storage procedures of the tip position information of the catheter for measurement according to the embodiment.

Before radiography in the reference data collection mode, an operator of the X-ray diagnosis apparatus 100 performs an input of information of the subject, settings of radiography conditions or image data creation conditions in the reference data collection mode and the support data creation mode, settings of the threshold α and the threshold β, settings of creation conditions of the support data for catheter treatment, selection of the reference data collection mode, or the like using the input unit 11 (Step S1 illustrated in FIG. 8), and mount the electrode for measurement of the electrocardiographic waveform measuring unit 132 onto a certain part of the subject 300 carried on the couchtop 6, in order to start measuring the electrocardiographic waveforms (Step S2 illustrated in FIG. 8). The various pieces of information that have been input, selected, or set through the input unit 11 are stored in the storage circuit included in the system controller 12.

Then, the operator inputs a radiography start instruction signal using the input unit 11 (Step S3 illustrated in FIG. 8). The instruction signal is provided to the system controller 12, whereby creation of the time-series image data in the reference data collection mode and detection of the tip position information of the catheter for measurement based on these pieces of image data are started.

That is to say, the system controller 12 that has received the radiography start instruction signal described above that has been input through the input unit 11 provides the X-ray irradiation conditions in the reference data collection mode included in the storage circuit of itself and an instruction signal for X-ray generation to the X-ray controller 51 of the high-voltage generation unit 5. The X-ray controller 51 that has received the instruction signals controls the high-voltage generator 52 based on the X-ray irradiation conditions to apply a high voltage to the X-ray tube 21 of the X-ray generation unit 2. The X-ray tube 21 to which the high voltage has been applied starts X-ray irradiation in the reference data collection mode with the scan field including the treatment target part of the subject 300. The X-ray transmitted through the scan field is detected by the plane detector 31 of the X-ray detection unit 3 provided rearward thereof.

In this respect, the photoelectric film of the detecting elements arranged in two dimensions in the plane detector 31 receives the X-ray transmitted through the scan field described above and accumulates the signal charge proportional to an amount of the X-ray transmitted on the charge accumulation capacitor. Once the X-ray irradiation in the predetermined time period ends, the gate driver 32 to which a clock pulse is provided from the system controller 12 provides a driving pulse to a TFT of the plane detector 31 to read out the signal charge accumulated in the charge accumulation capacitor.

The signal charge that has been read out described above is converted into a voltage in the charge-voltage converter 41 of the projection data creation unit 4, further converted into a digital signal in the A/D converter 42 to be once stored in a buffer memory of the parallel-serial converter 43 as the projection data for one line. Subsequently, the parallel-serial converter 43 reads out the projection data stored in the buffer memory of itself, in serial for each line to be stored in series in the projection data storage unit in the image data creation unit 8 to create two-dimensional image data, thereby creating two-dimensional image data. The image data obtained is displayed on the monitor of the display unit 10 (Step S4 illustrated in FIG. 8).

While sequentially moving the tip of the catheter for measurement, inserted with the catheter for treatment in the heart of the subject 300, along the surface of the cardiac muscle under observation of the image data displayed on the display unit 10, the operator measures the myocardial potential generated on the surface of the cardiac muscle using the catheter for measurement of the myocardial potential measuring unit 131 provided at the tip (Steps S5 and S6 illustrated in FIG. 8). Then, the operator place the tip of the catheter for measurement to a position in which the amplitude of the myocardial potential measured indicates a larger value than the threshold α that has been set in advance for a time period of a predetermined heartbeat period (one heartbeat period) (the treatment target part).

Once placement of the tip of the catheter for measurement based on the measurement result of the myocardial potential ends, the heartbeat time phase setting unit 99 of the data creation unit 9 sets the heartbeat time phase P1 of the subject 300 in the reference data collection mode based on the electrocardiographic waveforms provided from the electrocardiographic waveform measuring unit 132 (Step S7 illustrated in FIG. 8), whereby the information of the heartbeat time phase P1 that has been set is provided to the tip position information storage unit 92.

Each of the units included in the radiography unit 1 creates the image data of the heartbeat time phase P1 in the reference data collection mode using the same procedure as that of Step S4 described above (Step S8 illustrated in FIG. 8). The catheter tip detection unit 91 of the data creation unit 9 performs smoothing processing or outline highlight processing on the image data of the heartbeat time phase P1 provided from the image data creation unit 8, and further performs matching processing using the template data, or the like to detect the tip position information of the catheter for measurement (Step S9 illustrated in FIG. 8).

After that, the tip position information of the catheter for measurement detected by the catheter tip detection unit 91 based on the image data of the heartbeat time phase P1 is stored in the tip position information storage unit 92 with the heartbeat time phase P1 provided from the heartbeat time phase setting unit 99 as supplementary information (Step S10 illustrated in FIG. 8).

Once storage of the tip position information of the catheter for measurement in the heartbeat time phase P1 ends, in the same manner, the heartbeat time phase setting unit 99 detects the heartbeat time phases P2 through PN based on the electrocardiographic waveforms of the subject 300 provided from the electrocardiographic waveform measuring unit 132. The catheter tip detection unit 91 detects the tip position information of the catheter for measurement using the image data in the heartbeat time phases P2 through PN obtained by the radiography unit 1 and the image data creation unit 8. After that, the pieces of the tip position information obtained described above are stored in series in the tip position information storage unit 92 with the heartbeat time phases P2 through PN as supplementary information (Steps S7 through S10 illustrated in FIG. 8).

In the tip position information storage unit 92, however, as described above with reference to FIG. 6, only the tip position information of the catheter for measurement obtained in one heartbeat period of the time period [t3-t4], for example, in which the myocardial potential having the amplitude larger than the threshold α has been already measured is stored with the heartbeat time phases P1 through PN as supplementary information.

Creation Procedures of the Support Data for Catheter Treatment

Creation procedures of the support data for catheter treatment in the support data creation mode according to the embodiment will be described with reference to the flow-chart illustrated in FIG. 9.

Figure 9:
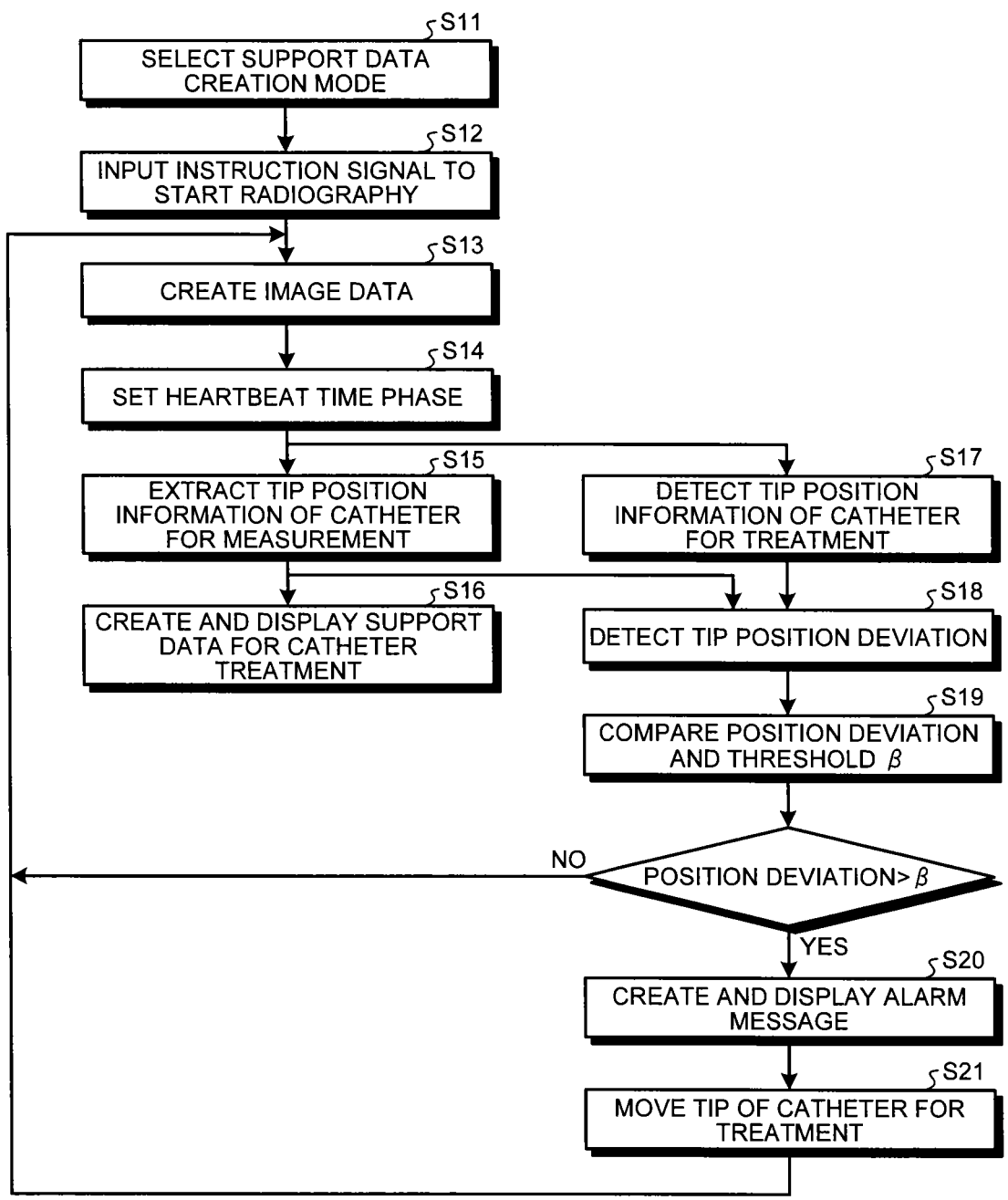
FIG. 9 is a flowchart illustrating creation procedures of support data for catheter treatment according to the embodiment.

Once the detection and storage of the tip position information of the catheter for measurement through the procedures illustrated in FIG. 8 ends, the operator selects the support data creation mode using the input unit 11 (Step S11 illustrated in FIG. 9) and further inputs the instruction signal to start radiography in the support data creation mode (Step S12 illustrated in FIG. 9). The instruction signal is provided to the system controller 12, whereby the image data of the heartbeat time phase Px in the support data creation mode is created.

That is to say, the system controller 12 that has received the radiography start instruction signal described above from the input unit 11 provides the X-ray irradiation conditions in the support data creation mode included in the storage circuit of itself and the instruction signal for X-ray generation to the radiography unit 1. The radiography unit 1 that has received the instruction signal stores the projection data created using the same procedure as that of Step S4 illustrated in FIG. 8 in the projection data storage unit of the image data creation unit 8 to create two-dimensional image data (Step S13 illustrated in FIG. 9). Then, the image data on which a predetermined image processing was performed in the image processing unit 95 is once stored in the image data storage unit 94 of the data creation unit 9.

The heartbeat time phase setting unit 99 of the data creation unit 9 receives the electrocardiographic waveforms of the subject 300 provided from the electrocardiographic waveform measuring unit 132 in parallel with creation of the image data described above and sets the heartbeat time phase (the heartbeat time phase of the image data) Px in creating the image data based on the electrocardiographic waveforms (Step S14 illustrated in FIG. 9).

Subsequently, the tip position information extraction unit 93 receives information of the heartbeat time phase Px provided from the heartbeat time phase setting unit 99 and extracts the tip position information of the catheter for measurement corresponding to the heartbeat time phase Px (i.e., detected in the heartbeat time phase that is the same as or the closest to the heartbeat time phase Px) out of the various pieces of tip position information stored in the tip position information storage unit 92 (Step S15 illustrated in FIG. 9).

Then, the support data creation unit 96 superimposes the tip position information of the catheter for measurement corresponding to the heartbeat time phase Px provided from the tip position information extraction unit 93 onto the image data in the support data creation mode that has been read out from the image data storage unit 94, thereby creating the support data for catheter treatment. After that, the support data creation unit 96 displays the support data for catheter treatment obtained on the monitor of the display unit 10 (Step S16 illustrated in FIG. 9).

The catheter tip detection unit 91 performs smoothing processing, outline highlight processing, pattern matching processing, or the like on the image data in the heartbeat time phase Px provided from the image data creation unit 8 in the support data creation mode to detect the tip position information of the catheter for treatment represented in the image data (Step S17 illustrated in FIG. 9).

The position deviation detection unit 97 detects position deviation between the tip of the catheter for treatment and the tip of the catheter for measurement in the heartbeat time phase Px based on the tip position information of the catheter for treatment detected by the catheter tip detection unit 91 in accordance with the image data of the heartbeat time phase Px that has been provided from the image data creation unit 8 almost in real time and the tip position information of the catheter for measurement corresponding to the heartbeat time phase Px of the image data provided from the tip position information extraction unit 93 (Step S18 illustrated in FIG. 9).

Then, the alarm signal creation unit 98 compares the detection result of the position deviation provided from the position deviation detection unit 97 and the threshold β that has been set in advance (Step S19 illustrated in FIG. 9). If the position deviation between the tips of the catheters is larger than the threshold β, the alarm signal creation unit 98 creates an alarm message in a predetermined format (alarm signal) to be displayed on the monitor of the display unit 10 (Step S20 illustrated in FIG. 9).

The operator of the X-ray diagnosis apparatus 100 who observed the alarm message displayed on the display unit 10 moves the tip of the catheter for treatment to the treatment target part, while referring to the image data in the support data creation mode represented in the support data for catheter treatment displayed on the display unit 10 at Step S16 described above and the tip position information of the catheter for measurement that is detected in the reference data collection mode and is superimposed onto the image data (Step S21 illustrated in FIG. 9).

Once creation and display of the support data for catheter treatment in the heartbeat time phase Px is performed, and creation and display of the alarm message and transfer of the tip of the catheter for treatment is performed as necessary, in the same manner, creation/display of the support data for catheter treatment based on the image data in the support data creation mode collected in other heartbeat time phase, creation/display of the alarm message, and transfer of the tip of the catheter for treatment are performed in series (Steps S13 through S21 illustrated in FIG. 9). Furthermore, the catheter treatment based on the support data for catheter treatment obtained is performed on the treatment target part of the subject 300.

Modification

A modification of the data creation unit 9 included in the X-ray diagnosis apparatus 100 according to the embodiment will be described. The data creation unit in the modification according to the embodiment performs radiography in the reference data collection mode in the heartbeat time phases P1 through PN in a predetermined heartbeat period in a state in which the tip of the catheter for measurement that specifies the treatment target part through measurement of the myocardial potential is placed on the treatment target part, to create the time-series image data. The data creation unit detects the tip position information of the catheter for measurement represented in each of the pieces of these image data, thereby creating the tip trace data.

Subsequently, the data creation unit performs radiography in the support data creation mode in a state in which the tip of the catheter for treatment that has been inserted with the catheter for measurement described above in the heart of the subject on the purpose of ablation treatment is placed in the vicinity of the treatment target part. The data creation unit superimposes the tip trace data of the catheter for measurement described above onto the image data obtained, thereby creating the support data for catheter treatment effective for ablation treatment.

The structure and functions of the data creation unit in the modification according to the embodiment will now be described with reference to FIG. 10. In the block diagram of FIG. 10 illustrating the structure of the data creation the data creation unit, the units having the same structure and functions as those of the units of the data creation unit 9 illustrated in FIG. 3 are designated by the same reference numerals and detailed explanation thereof will be omitted.

Figure 10:
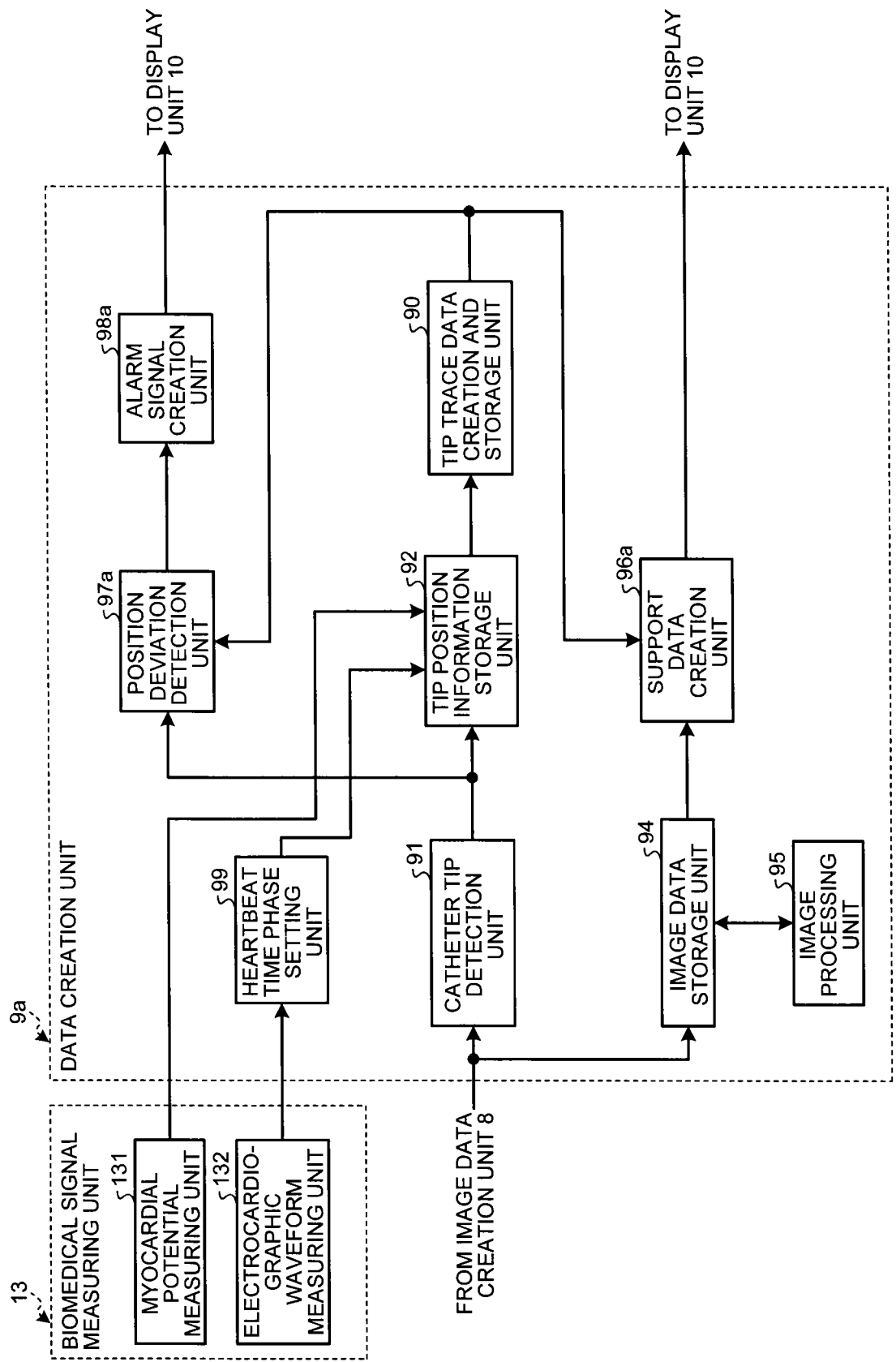
FIG. 10 is a block diagram illustrating a specific structure of the data creation unit in a modification according to the embodiment.

A data creation unit 9a in the modification according to the embodiment illustrated in FIG. 10 includes the catheter tip detection unit 91, the tip position information storage unit 92, the image data storage unit 94, the image processing unit 95, and the heartbeat time phase setting unit 99, each of which has almost the same structure and functions as the embodiment described above, and further includes a tip trace data creation and storage unit 90, a support data creation unit 96a, a position deviation detection unit 97a, and an alarm signal creation unit 98a. The tip trace data creation and storage unit 90 creates tip transfer trace data of the catheter for measurement (hereinafter, referred to as tip trace data) based on the tip position information that has been read out from the tip position information storage unit 92. The support data creation unit 96a creates the support data for catheter treatment by composing the tip trace data of the catheter for measurement obtained and the image data in the support data creation mode. The position deviation detection unit 97a detects the position deviation of the tip of the catheter for treatment with respect to the tip of the catheter for measurement (i.e., the treatment target part) based on the tip position information of the catheter for treatment represented in the image data in the support data creation mode and the tip trace data of the catheter for measurement described above. The alarm signal creation unit 98a creates an alarm signal based on a comparative result of the position deviation and a predetermined threshold γ.

The tip trace data creation and storage unit 90 includes a trace data creation unit and a trace data storage unit not illustrated. The trace data creation unit reads out the tip position information of the catheter for measurement stored in the tip position information storage unit 92 with the heartbeat time phases P1 through PN detected by the catheter tip detection unit 91 as supplementary information to create the tip trace data represented with, for example, a curve or a closed-loop. The tip trace data of the catheter for measurement obtained is stored in the trace data storage unit.

The support data creation unit 96a includes a data addition unit not illustrated and superimposes the tip trace data of the catheter for measurement provided from the trace data storage unit of the tip trace data creation and storage unit 90 onto the image data in the support data creation mode provided from the image data storage unit 94 almost in real time, thereby creating the support data for catheter treatment.

The position deviation detection unit 97a includes the distance measuring unit not illustrated. When the support data for catheter treatment described above is created in the support data creation mode, the position deviation detection unit 97a detects the position deviation of the tip of the catheter for treatment with respect to the tip of the catheter for measurement (i.e., the treatment target part) based on the tip position information of the catheter for treatment detected by the catheter tip detection unit 91 in accordance with the image data in the support data creation mode provided from the image data creation unit 8 almost in real time and the tip trace data of the catheter for measurement provided from the trace data storage unit of the tip trace data creation and storage unit 90.

Figure 11:
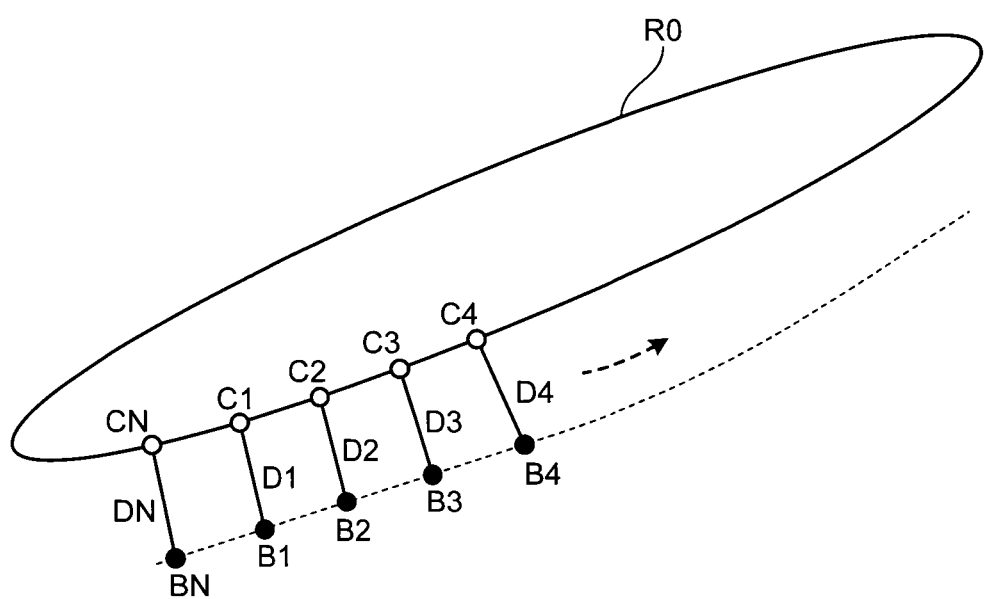
FIG. 11 is a diagram for explaining position deviation detection of a catheter tip in the modification according to the embodiment.

FIG. 11 is a diagram for explaining detection of position deviation of the catheter tip performed by the position deviation detection unit 97a. The closed-loop R0 represents the tip trace data created by the tip trace data creation and storage unit 90 based on the tip position information of the catheter for measurement in the heartbeat time phases P1 through PN in the reference data collection mode. B1, B2, B3, through BN, respectively, represent the tip position information of the catheter for treatment in the heartbeat time phases P1, P2, P3, through PN in the support data creation mode detected by the catheter tip detection unit 91.

The distance measuring unit of the position deviation detection unit 97a to which the tip position information of the catheter for treatment B1 through BN and the tip trace data of the catheter for measurement R0 are provided form the catheter tip detection unit 91 and the tip trace data creation and storage unit 90 firstly detects C1 on the closed-loop R0 that is the closest to the tip position information B1, then measures D1 that is a distance between B1 and C1. In the same manner, the distance measuring unit detects C2, C3, through CN on the closed-loop R0 that is the closest to the tip position information B2, B3, through BN, then measures D2 that is a distance between B2 and C2, D3 that is a distance between B3 and C3, and through DN that is a distance between BN and CN in series.

The alarm signal creation unit 98a illustrated in FIG. 10 has a data comparison unit and an alarm message creation unit not illustrated. The data comparison unit compares distances D1 through DN provided from the position deviation detection unit 97a and the threshold γ that has been set in advance. If some of the measurements consecutive in the distances D1 through DN are larger than the threshold γ a predetermined number of times consecutively, the alarm message creation unit creates a predetermined alarm message (alarm signal) to be provided to the display unit 10.

Measurement of distance is not limited to the method described above. For example, the tip position information of the catheter for measurement and the tip position information of the catheter for treatment do not necessarily have the same heartbeat time phases. In this case, for example, the distance measuring unit of the position deviation detection unit 97a may detect more accurately position relationships of the tip position information of the catheter for treatment B1 through BN and the tip position information of the catheter for measurement C1 through CN based on the heartbeat time phase information of the subject. For example, the tip position information of the catheter for treatment B2 is detected in the heartbeat time phase in the middle point between the heartbeat time phases P1 and P2. In this case, the distance measuring unit detects a position of the tip position information B2 corresponding to the heartbeat time phase on the closed-loop R0 based on the heartbeat time phases P1 through PN added to the tip position information of the catheter for measurement C1 through CN. In the example described above, for example, the corresponding position is a position in the middle point between the C1 and C2. Therefore, the distance measuring unit may measure the distance between the tip position information of the catheter for treatment B2 and the middle point of the C1 and C2. In this case, for the threshold used for comparison by the data comparison unit, less value can be used as a result of improvement of accuracy.

Creation and Storage Procedures of the Tip Trace Data

Figure 12:
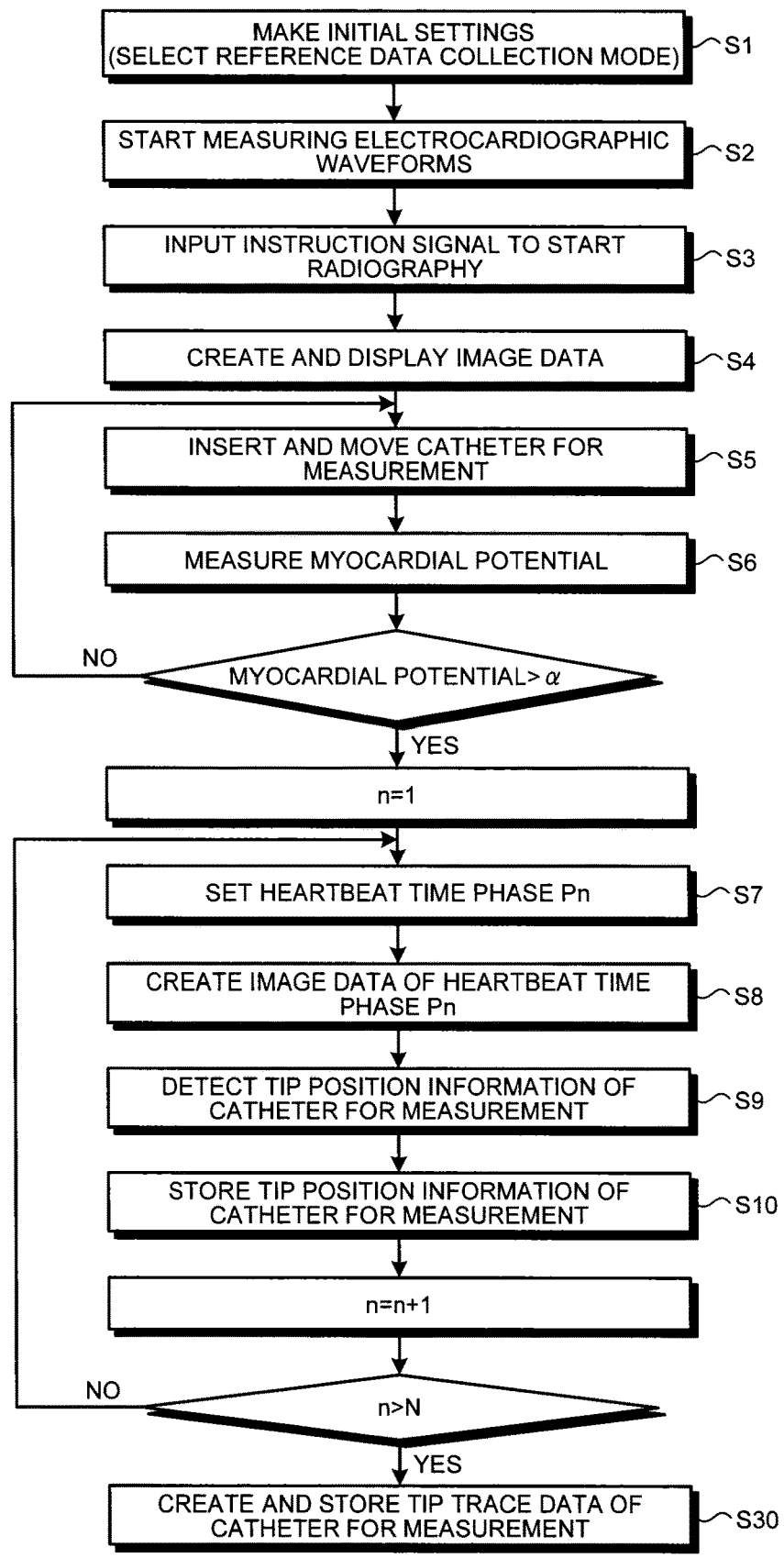
FIG. 12 is a flowchart illustrating creation and storage procedures of tip trace data of the catheter for measurement in the modification according to the embodiment.

Creation and storage procedures of the tip trace data in the reference data collection mode of the modification with reference to the flowchart illustrated in FIG. 12. In the flowchart illustrated in FIG. 12 representing creation and storage procedures of the tip trace data, the same steps as Steps of detection and storage procedures of the tip position information illustrated in FIG. 8 are designated by the same reference numerals and explanation thereof will be omitted.

Once detection and storage of the tip position information of the catheter for measurement in the heartbeat time phases P1 through PN through the same procedures as Steps S1 through S10 illustrated in FIG. 8 ends, the trace data creation unit of the tip trace data creation and storage unit 90 included in the data creation unit 9a reads out the tip position information of the catheter for measurement in the heartbeat time phases P1 through PN stored in the tip position information storage unit 92 and creates the tip trace data represented with a linear or closed loop. Then, the trace data creation unit stores the tip trace data of the catheter for measurement obtained in the trace data storage unit of the tip trace data creation and storage unit 90 (Step S30 illustrated in FIG. 12).

Creation Procedures of the Support Data for Catheter Treatment

Figure 13:
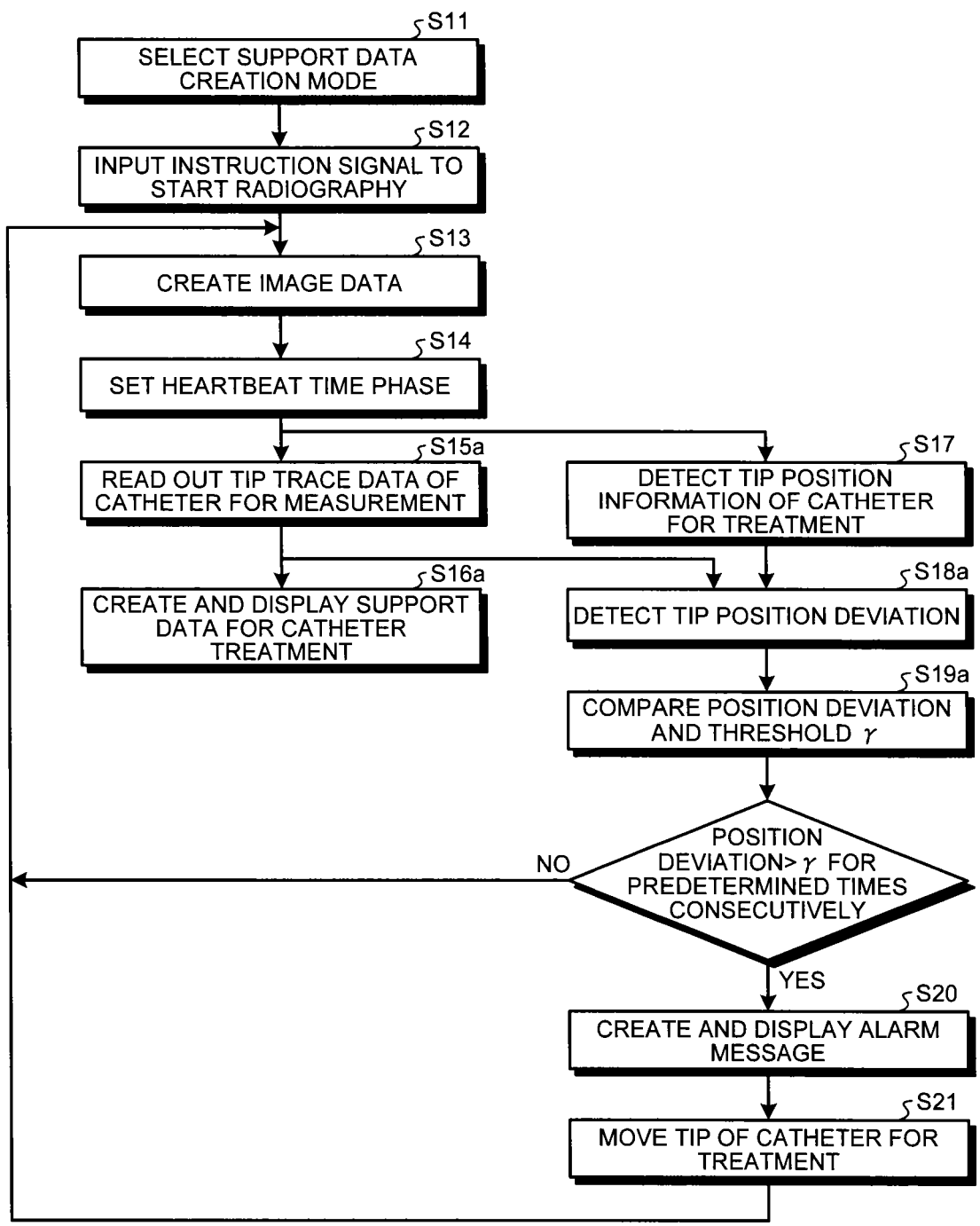
FIG. 13 is a flowchart illustrating creation procedures of the support data for catheter treatment in the modification according to the embodiment.

The following describes creation procedures of the support data for catheter treatment in the support data creation mode of the modification with reference to the flowchart illustrated in FIG. 13. In the flowchart illustrated in FIG. 13 representing creation procedures of the support data for catheter treatment, the same steps as Steps of creation procedures of the support data for catheter treatment in FIG. 9 are designated by the same reference numerals and explanation thereof will be omitted.

Through the same steps as Steps S11 through S14 illustrated in FIG. 9, once the settings of the heartbeat time phase Px in the support data creation mode and creation of the image data in the heartbeat time phase Px ends, the support data creation unit 96a of the data creation unit 9a reads out the tip trace data of the catheter for measurement stored in the trace data storage unit of the tip trace data creation and storage unit 90 (Step S15a illustrated in FIG. 13). Then, the support data creation unit 96a superimposes the tip trace data of the catheter for measurement onto the image data in the support data creation mode provided from the image data storage unit 94 almost in real time, thereby creating the support data for catheter treatment. After that, the support data creation unit 96a displays the support data for catheter treatment obtained on the monitor of the display unit 10 (Step S16a illustrated in FIG. 13).

The catheter tip detection unit 91 performs a predetermined processing on the time-series image data provided from the image data creation unit 8 in the support data creation mode to detect the tip position information of the catheter for treatment represented in the image data (Step S17 illustrated in FIG. 13).

The position deviation detection unit 97a detects a distance (position deviation) between the tip position information of the catheter for treatment detected by the catheter tip detection unit 91 in a plurality of heartbeat time phases in accordance with the image data in the support data creation mode provided from the image data creation unit 8 in a time-series manner and almost in real time and the tip trace data of the catheter for measurement provided from the tip trace data creation and storage unit 90 (Step S18a illustrated in FIG. 13).

Then, the alarm signal creation unit 98a compares the position deviation provided from the position deviation detection unit 97a and the threshold γ that has been set in advance (Step S19a illustrated in FIG. 13). If values of the position deviation are larger than the threshold γ a predetermined number of times consecutively, the alarm signal creation unit 98a creates a predetermined alarm message (alarm signal) to be displayed on the display unit 10 (Step S20 illustrated in FIG. 13).

The operator of the X-ray diagnosis apparatus 100 who observed the alarm message displayed on the display unit 10 moves the tip of the catheter for treatment to a position close to the treatment target part based on the image data represented in the support data for catheter treatment displayed at Step S16a described above and the tip trace data of the catheter for measurement that is superimposed onto the image data (Step S21 illustrated in FIG. 13).

The X-ray irradiation field in radiography in creation of the image data illustrated at Step S13 in FIG. 13 is set based on the tip trace data of the catheter for measurement provided from the tip trace data creation and storage unit 90. By narrowing the X-ray irradiation field in the support data creation mode than the X-ray irradiation field in the reference data collection mode, exposed dose on the subject 300 under the catheter treatment can be reduced.

According to the embodiment and the modification thereof in the present disclosure described above, when the catheter treatment is performed on the cardiac muscle or the like while the X-ray image data is observed, the position deviation of the tip of the catheter for treatment from the tip of the catheter for measurement (i.e., the treatment target part) can be readily recognized by superimposing and displaying the tip position information of the catheter for measurement (transfer trace information) specifying the position of the treatment target part that has been detected in advance while being placed in or in a preferable position in the vicinity of the treatment target part onto the image data in the support data creation mode representing the catheter for treatment on the purpose of the treatment target part. As a result, the position deviation of the tip of the catheter for treatment with respect to the treatment target part can be readily corrected, whereby safety and secured catheter treatment can be performed.

The exposed dose on the subject can be reduced by controlling the placement of the diaphragm blades included the variable diaphragm in the X-ray generation unit based on the tip position information of the catheter for measurement so that the irradiation range of radiography is limited to the treatment target part existing in the vicinity of the tip of the catheter for measurement.

Furthermore, if the position deviation of the tip of the catheter for treatment from the tip of the catheter for measurement (the treatment target part) is large, by displaying the alarm message (alarm signal) created in a predetermined format, the position deviation of the tip of the catheter for treatment can be corrected securely.

According to the modification described above, by creating the tip trace data based on a plurality of pieces of tip position information of the catheter for measurement detected in a predetermined the heartbeat period and superposing the tip trace data obtained onto the image data in the support data creation mode representing the catheter for treatment to be displayed, information on a transfer direction, a transfer range, or the like of the treatment target part along with heartbeats can be recognized accurately, and the position deviation of the tip of the catheter for treatment can be corrected more readily.

While certain embodiments and modifications have been described, these embodiments and modifications are presented by way of example only, and are not intended to limit the scope of this disclosure. Indeed, the novel methods and systems described herein may be embodied in a variety of other forms. For example, in the embodiment above, although an example in which arrhythmia is removed by performing ablation treatment on the treatment target part on the surface of the cardiac muscle using the catheter for treatment has been described. However, treatment using the catheter for treatment is not limited to the example described above.

In the embodiment described above, an example in which the tip position information of the catheter for measurement measured in the heartbeat time phase that is the same as or the closest to the heartbeat time phase of the image data is superimposed onto the image data in the support data creation mode has been described above. In the modification described above, an example in which the tip trace data created based on a plurality of pieces of tip position information of the catheter for measurement measured in one heartbeat period is superimposed onto the image data has been described. However, the tip position information and the tip trace data described above may be superimposed onto the image data in the support data creation mode. According to this method, the transfer direction and the transfer range of the treatment part in a predetermined heartbeat period, and a position relationship with respect to the tip of the catheter for treatment and the treatment target part in the heartbeat period can be recognized readily. The time period in which the tip position information of the catheter for measurement is measured is not limited to one heartbeat period and a plurality of heartbeat periods are permissible.

In the embodiment described above, an example in which the repetition frequency of the X-ray irradiation in the reference data collection mode is set higher than the repetition frequency of the X-ray irradiation in the support data creation mode, in order to accurately detect the tip position information of the catheter for measurement has been described. However, for example, the tip position information of the catheter for measurement with superior continuity may be collected by performing interpolation processing on the tip position information of the catheter for measurement detected with a repetition frequency of the X-ray irradiation equal to the repetition frequency of the X-ray irradiation in the support data creation mode.

According to the embodiment and the modification thereof described above, an example in which one piece of the tip position information or one piece of the tip trace data is superimposed onto the image data in the support data creation mode to be displayed has been described. However, a plurality of pieces of tip position information or a plurality of pieces of tip trace data may be superimposed to be displayed instead. In this case, each of a plurality of pieces of tip position information or a plurality of pieces of tip trace data is displayed using different hue, brightness, a degree of transparency, and the like, whereby a plurality of pieces of tip position information or a plurality of pieces of tip trace data can be readily associated with the tip of the catheter for treatment represented in the image data in the support data creation mode.

An example in which the alarm message created based on the position deviation between the tip of the catheter for treatment and the tip of the catheter for measurement, and the image data in the support data creation mode are displayed on the same display unit 10 has been described. However, the alarm message may be displayed on another display provided separately or on a display panel of the input unit 11, for example. The alarm signal created by the alarm signal creation unit 98 is not limited to the alarm message described above. For example, a lamp signal flashing or an audio signal may be permissible.

An example in which position measurement and treatment on the treatment target part using the catheter for measurement and the catheter for treatment independent to each other has been described above. However, the catheter for measurement and the catheter for treatment may be integrally structured. In addition, although the X-ray diagnosis apparatus 100 including the myocardial potential measuring unit 131 and the electrocardiographic waveform measuring unit 132 has been described, the myocardial potential measuring unit 131 and the electrocardiographic waveform measuring unit 132 may be provided independent from the X-ray diagnosis apparatus 100.

The data creation unit 9 or the like included in the X-ray diagnosis apparatus 100 according to the embodiment can be achieved by using, for example, a computer including a CPU, a random access memory (RAM), a magnetic storage device, an input device, a display device, and the like as hardware. For example, the system controller 12 that controls the data creation unit 9 can achieve various functions by making a processor such as a CPU mounted on the computer described above execute a predetermined control program. In this example, the control program described above may be installed in a computer in advance, or the control program stored in a computer-readable storage medium or distributed over a network may be installed in a computer.

The embodiment described above can be applied to a bi-plane X-ray diagnosis apparatus in the same manner. In general, in the bi-plane X-ray diagnosis apparatus, a front imaging system that images the subject carried on a couchtop on its back from the front and a side imaging system that images the subject from the side are installed to enable simultaneously imaging from two directions. The front imaging system includes a C-arm supported with a stand placed on a floor and an X-ray generation unit and an X-ray detection unit installed at the both ends of the C-arm, for example. The side imaging system includes an Ω arm suspended from a ceiling, an elevator mechanism provided at the both ends of the Ω arm, and the X-ray generation unit and the X-ray detection unit supported with the elevator mechanism.

For example, the support data creation unit superimposes the tip position information or the tip trace data of the catheter for measurement onto the image data in the support data creation mode provided for each of the two imaging systems, thereby creating the support data for catheter treatment in each system. The display unit creates display data from pieces of support data for catheter treatment to be displayed on the monitor. FIG. 14 illustrates a specific example of the support data for catheter treatment created in another embodiment. In FIG. 14, an example representing the support data for catheter treatment onto which the tip trace data is superimposed is illustrated. Although in FIG. 14, other information (e.g., an alarm message or information of a subject) or a part of the catheter information is omitted, the display unit may display such information. As described above, when the embodiment is applied to the bi-plane X-ray diagnosis apparatus, the support data for catheter treatment in at least two directions and information in a depth direction or the like can be provided. Therefore, the observer can recognize more accurately the position deviation of the tip of the catheter for treatment from the treatment target part.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus, comprising:
an X-ray tube configured to irradiate a treatment target part of a subject with an X-ray;
an X-ray detector configured to detect the X-ray transmitted through the subject and output a signal; and
processing circuitry configured to
generate a sequence of images in a time-series manner based on the signal during one period of a heartbeat of the subject;
detect a position of a tip of a catheter, which moves due to the heartbeat of the subject, in each of the sequence of images;
store, in a memory, transfer trace information including the detected position of the tip of the catheter in each of the sequence of images;
create tip trace data representing positions of the tip at a plurality of time points during the period of the heartbeat by generating a curve or a closed loop by tracing the positions of the detected tip of the catheter based on the stored transfer trace information, the tip trace data representing the curve or the closed loop;
superimpose the generated curve or the closed loop onto present image data to create support data; and
cause a display to display the support data.

2. The X-ray diagnosis apparatus according to claim 1, wherein the processing circuitry is further configured to:
create the tip trace data by extracting the transfer trace information of the tip of the catheter during the heartbeat with a heartbeat time phase as supplementary information out of various transfer trace information stored in the memory.

3. The X-ray diagnosis apparatus according to claim 2, wherein the processing circuitry is further configured to set the heartbeat time phase based on electrocardiographic waveforms in the period of the heartbeat collected from the subject, and
add the heartbeat time phase to the transfer trace information of the tip of the catheter in each heartbeat time phase and store the resulting information in the memory.

4. The X-ray diagnosis apparatus according to claim 1, wherein the processing circuitry is further configured to store, in the memory, the transfer trace information in the period of the heartbeat detected in a time period in which myocardial potential collected from the treatment target part indicates a larger value than a predetermined threshold.

5. The X-ray diagnosis apparatus according to claim 1, wherein the processing circuitry is further configured to
detect position deviation between a catheter for measurement specifying a position of the treatment target part and a catheter for treatment performing treatment on the treatment target part, based on tip position information of the catheter, and
create an alarm signal when the position deviation is larger than a threshold.

6. The X-ray diagnosis apparatus according to claim 1, further comprising an X-ray controller configured to control a repetition frequency of the X-ray irradiation in a reference data collection mode in which tip position information of the catheter for measurement specifying a position of the treatment target part is detected and in a support data creation mode in which the support data is created, wherein
the X-ray controller is further configured to set the repetition frequency of the X-ray irradiation in the reference data collection mode higher than the repetition frequency of the X-ray irradiation in the support data creation mode.

7. The X-ray diagnosis apparatus according to claim 1, wherein the processing circuitry is further configured to cause the display to display the tip trace data using a color tone, a brightness, or a degree of transparency different from that of the image data onto which the tip trace data is superimposed.

8. The X-ray diagnosis apparatus according to claim 1, wherein
the X-ray diagnosis apparatus is a bi-plane X-ray diagnosis apparatus configured to perform imaging from two directions at the same time, and
the processing circuitry is further configured to cause the display to display each piece of the support data in which the tip trace data is superimposed onto each piece of image data imaged from the two directions.

9. A control method, comprising:

generating a sequence of images in a time-series manner based on a signal outputted from an X-ray detector detecting an X-ray irradiated by an X-ray tube and transmitted through a subject during a one period of a heartbeat of the subject;

detecting a position of a tip of a catheter, which moves due to the heartbeat of the subject, in each of the sequence of images;

storing, in a memory, transfer trace information including the detected position of the tip of the catheter in each of the sequence of images;

creating tip trace data representing positions of the tip at a plurality of time points during the period of the heartbeat by generating a curve or a closed loop by tracing positions of the detected tip of the catheter based on the stored transfer trace information of the tip of the catheter, the tip trace data representing the curve or the closed loop;

superimposing the generated curve or the closed loop onto present image data to create support data; and displaying the support data on a display.

10. An X-ray diagnosis apparatus, comprising:

an X-ray tube configured to irradiate a treatment target part of a subject with an X-ray;

an X-ray detector configured to detect the X-ray transmitted through the subject and output a signal; and processing circuitry configured to generate a sequence of images in a time-series manner based on the signal during one period of a heartbeat of the subject;

detect a position of a tip of a catheter, which moves due to the heartbeat of the subject, in each of the sequence of images;

store, in a memory, transfer trace information including the detected position of the tip of the catheter in each of the sequence of images;

create tip trace data representing positions of the tip at a plurality of time points during the period of the heartbeat by generating a smooth closed loop by tracing the positions of the detected tip of the catheter based on the stored transfer trace information, the tip trace data representing the smooth closed loop;

superimpose the generated smooth closed loop onto present image data to create support data; and cause a display to display the support data.

* * * * *